(12) United States Patent
Remington et al.

(10) Patent No.: US 7,015,310 B2
(45) Date of Patent: Mar. 21, 2006

(54) OXIDATION REDUCTION SENSITIVE GREEN FLUORESCENT PROTEIN VARIANTS

(75) Inventors: S. James Remington, Eugene, OR (US); George T. Hanson, Madison, WI (US)

(73) Assignee: The State of Oregon Acting by and through the State Board of Higher Education on Behalf of the University of Oregon, Eugene, OR (US)

( * ) Notice: Subject to any disclaimer, the term of this patent is extended or adjusted under 35 U.S.C. 154(b) by 0 days.

(21) Appl. No.: 10/471,857

(22) PCT Filed: Mar. 11, 2002

(86) PCT No.: PCT/US02/07374

§ 371 (c)(1),
(2), (4) Date: Mar. 8, 2004

(87) PCT Pub. No.: WO02/077011

PCT Pub. Date: Oct. 3, 2002

(65) Prior Publication Data

US 2004/0171112 A1    Sep. 2, 2004

Related U.S. Application Data

(60) Provisional application No. 60/275,200, filed on Mar. 12, 2001, provisional application No. 60/293,427, filed on May 23, 2001, provisional application No. 60/302,894, filed on Jul. 3, 2001.

(51) Int. Cl.
*C07K 1/00* (2006.01)

(52) U.S. Cl. ............... 530/350; 530/300; 530/350; 435/7.1; 435/69.1; 435/325; 435/252.3; 435/320.1; 514/2; 514/12; 514/21

(58) Field of Classification Search ............... 530/350, 530/300; 435/7.1, 69.1, 325, 252.3, 320.1; 514/12, 2, 21
See application file for complete search history.

(56) References Cited

U.S. PATENT DOCUMENTS

| | | | |
|---|---|---|---|
| 5,565,323 A | 10/1996 | Parker et al. | |
| 5,625,048 A | 4/1997 | Tsien et al. | |
| 5,777,079 A | 7/1998 | Tsien et al. | |
| 5,804,387 A | 9/1998 | Cormack et al. | |
| 5,874,304 A | 2/1999 | Zolotukhin et al. | |
| 5,888,498 A | 3/1999 | Davis et al. | |
| 5,908,747 A | 6/1999 | Shibata et al. | |
| 5,912,137 A | 6/1999 | Tsien et al. | |
| 5,968,738 A | 10/1999 | Anderson et al. | |
| 5,968,750 A | 10/1999 | Zolotukhin et al. | |
| 5,994,077 A | 11/1999 | Valdivia et al. | |
| 6,020,192 A | 2/2000 | Muzyczka et al. | |
| 6,054,321 A | 4/2000 | Tsien et al. | |
| 6,066,476 A | 5/2000 | Tsien et al. | |
| 6,077,707 A | 6/2000 | Tsien et al. | |
| 6,090,919 A | 7/2000 | Cormack et al. | |
| 6,096,865 A | 8/2000 | Michaels | |
| 6,124,128 A | 9/2000 | Tsien et al. | |
| 6,140,132 A | 10/2000 | Tsien et al. | |
| 6,146,826 A | 11/2000 | Chalfie et al. | |
| 6,172,188 B1 | 1/2001 | Thastrup et al. | |
| 6,306,600 B1 | 10/2001 | Kain et al. | |
| 6,316,181 B1 | 11/2001 | Fillmore et al. | |
| 6,319,669 B1 | 11/2001 | Tsien et al. | |
| 6,342,379 B1 | 1/2002 | Tsien et al. | |
| 6,414,119 B1 | 7/2002 | Fisher | |
| 6,509,174 B1 | 1/2003 | Jordan et al. | |
| 6,803,188 B1 * | 10/2004 | Tsien et al. .................. 435/6 |
| 2002/0123113 A1 | 9/2002 | Tsien et al. | |
| 2003/0017538 A1 | 1/2003 | Miyawaki et al. | |

FOREIGN PATENT DOCUMENTS

| WO | WO 96/23810 | 8/1996 |
|---|---|---|
| WO | WO 98/02571 | 1/1998 |
| WO | WO 99/64592 | 12/1999 |

OTHER PUBLICATIONS

Akerley et al., "Systematic identification of essential genes by in vitro mariner mutagenesis," *Proc. Natl. Acad. Sci. USA*, 95:8927-8932, Jul. 1998.

Arai et al., "Mitochondrial Phospholipid Hydroperoxide Glutathione Peroxidase Plays a Major Role in Preventing Oxidative Injury in Cells," *J. Biological Chemistry*, 274(8):4924-4933, 1999.

Chattoraj et al., "Ultra-fast excited dynamics in green fluorescent protein: Multiple states and proton transfer," *Proc. Natl. Acad. Sci. USA*, 93:8362-8367, Aug. 1996.

(Continued)

Primary Examiner—Kathleen M. Kerr
Assistant Examiner—Hope Robinson
(74) Attorney, Agent, or Firm—Klarquist Sparkman LLP

(57) ABSTRACT

The disclosure provides proteins that can be used to determine the redox status of an environment (such as the environment within a cell or subcellular compartment). These proteins are green fluorescent protein (GFP) variants (also referred to as redox sensitive GFP (rosGFP) mutants), which have been engineered to have two cysteine amino acids near the chromophore and within disulfide bonding distance of each other. Also provided are nucleic acid molecules that encode rosGFPs, vectors containing such encoding molecules, and cells transformed therewith. The disclosure further provides methods of using the rosGFPs (and encoding molecules) to analyze the redox status of an environment, such as a cell, or a subcellular compartment within a cell. In certain embodiments, both redox status and pH are analyzed concurrently.

26 Claims, 17 Drawing Sheets

OTHER PUBLICATIONS

Coxon and Bestor, "Proteins that glow in green and blue," *Chemistry & Biology*, 2:119-121, 1995.

Gustaffson et al., "Identification of new RNA modifying enzymes by iterative genome search using known modifying enzymes as probes," *Nucleic Acids Research*, 24(19):3756-3762, 1996.

Inouye and Tsuji, "Evidence for redox forms of the *Aequorea* green fluorescent protein," *FEBS Letters* 351:211-214, 1994.

Ná ray-Fejes-Tóth et al., "Subcellular Localization of the Type 2 11β-Hydroxysteriod Dehydrogenase," *J. Biological Chemistry*, 271(26):15436-15442, 1996.

Niwa et al., "Chemical nature of the light emitter of the *Aequorea* green fluorescent protein," *Proc. Natl. Acad. Sci. USA*, 93:13617-13622, Nov. 1996.

Li et al., "Generation of Destabilized Green Fluorescent Protein as a Transcription Reporter," *J. Biological Chemistry*, 273(52):34970-34975, 1998.

"Living Colors® User Manual," *Clontech*, 51 pp., Apr. 2, 1999.

Okamato et al., "Redox-dependent Regulation of Nuclear Import of the Glucocorticoid Receptor," *J. Biological Chemistry*, 274(15):10363-10371, 1999.

Reichel et al., Enhanced green fluorescence by the expression of an *Aequorea victoria* green fluorescent protein mutant in mono- and dicotyledonous plant cells, *Pro. Natl. Acad. Sci. USA*, 93:5888-5893, Jun. 1996.

Siemering et al., "Mutations that suppress the thermosensitivity of green fluorescent protein," *Current Biology*, 6(12):1653-1663, 1996.

Simpson et al., "Systematic subcellular localization of novel proteins identified by large-scale cDNA sequencing," *EMBO Reports*, 1(3):287-292, 2000.

Stearns, "The green revolution," *Current Biology*, 5:262-264, 1995.

Wachter and Remington, "Sensitivity of the yellow variant of green fluorescent protein to halides and nitrate," *Current Biology* 9(17):628-629, 1999.

"*Aequorea victoria* green fluorescent protein mRNA complete cds" GenBank Accession M62653, Apr. 26, 1993.

"*Aequorea victoria* green-fluorescent protein mRNA complete cds," GenBank Accession M62654, Apr. 26, 2003.

"Clontech GFP License Statements," *Clontech*, www.clontech.com/gfp/license/index.html, 2 pp., accessed Nov. 26, 2000.

"The Fluorophore of Green Fluorescent Protein," pps99.cryst.bbk.ac.uk/projects/gmocz/gfp.htm, 6 pp., accessed Nov. 18, 2000.

"Illuminating the Structure of Green Fluorescent Protein," *NPACI Online*, www.npaci.edu/online/v4.14/gfp.html, IV:14, 4 pp., accessed Jul. 12, 2000.

"Living Colors™ Fluorescent Proteins," *Clontech*, www.clontech.com/gfp/, accessed Nov. 18, 2000.

"Patent mutations for improved performance, " *Amersham Biosciences*, www5.amershambiosciences.com/aptrix/upp00919.nsf/content/D9B3F40CB359B9B, 5 pp., accessed Mar. 12, 2003.

"Product Catalog: N-Terminal Enhanced Fluorescent Protein Vectors," *Clontech*, www.clontech.com/products/catalog01/Sec5/p178nterminalefpv.html, 3 pp., accessed Jan. 13, 2001.

\* cited by examiner

OXIDATION REDUCTION SENSITIVE GREEN FLUORESCENT PROTEIN VARIANTS

CROSS REFERENCE TO RELATED APPLICATIONS

This is a § 371 U.S. National Stage of International Application No. PCT/US02/07374, filed Mar. 11, 2002 (published in English under PCT Article 21(2)), which in turn claims the benefit of U.S. Provisional Patent Application Nos. 60/275,200, filed Mar. 12, 2001, 60/293,427, filed May 23, 2001, and 60/302,894, filed Jul. 3, 2001.

STATEMENT OF GOVERNMENT RIGHTS

This invention was made with government support under grant number GM07759-22 and grant number GM42618-10 both awarded by the National Institutes of Health (NIH). The government has certain rights in the invention.

FIELD

The present disclosure relates to the field of genetic engineering, and in particular to green fluorescent protein (GFP) mutants that can be used to detect oxidation-reduction state, or a change in oxidation-reduction state.

BACKGROUND

The green fluorescent protein (GFP) from the Pacific Northwest jellyfish, *Aequorea victoria*, has been used extensively in molecular and cell biology as a fluorescent marker. It is a 238 amino acid protein that generates its own fluorescent chromophore. The spontaneous generation of the chromophore is achieved by cyclization of the internal Ser65-Tyr66-Gly67 sequence followed by oxidation of Tyr 66 in the presence of molecular oxygen (Heim et al., *Proc. Natl. Acad. Sci. USA* 91:12501–12504, 1994). The overall fold of the protein consists of an 11-stranded β-barrel capped by α-helices at both ends and contains a coaxial α-helix from which the chromophore is generated (Brejc et al., *Proc. Natl. Acad. Sci. USA* 94:2306–2311, 1997; Ormö et al., *Science* 273:1392–1395, 1996; Yang et al., *Nat. Biotech.* 14:1246–1251, 1996). GFP is unique among light emitting proteins, because it does not require the presence of any cofactors or substrates for the production of green light.

Wild-type GFP has absorption maxima at 398 and 475 nm (Morise et al., *Biochemistry* 13:2656–2662, 1974). Excitation at either of these wavelengths leads to emission of green light at 508 nm (Morise et al., 1974). The usefulness of GFP has been greatly enhanced by the availability of mutants with a broad range of absorption and emission maxima (Heim et al., *Proc. Natl. Acad. Sci. USA* 91:12501–12504, 1994; Ormö et al., *Science* 273:1392–1395, 1996). These mutants have made possible multicolor reporting of cellular processes by allowing for the simultaneous observation of two or more gene products labeled with different colored GFP variants (Rizzuto et al., *Curr. Biol.* 6:183–188, 1996). In addition, fluorescence resonance energy transfer (FRET) experiments using different colored GFP's have been used to study protein-protein interactions in vivo (Heim et al., *Curr. Biol.* 6:178–182, 1996; Mitra et al., *Gene* 173:13–17, 1996).

More recently, GFP variants have been shown to be sensitive to pH (Wachter et al., *Biochemistry* 36:9759–9765, 1997; Elsliger et al., *Biochemistry* 38:5296–5301, 1999). As a consequence, they have been used as noninvasive intracellular pH indicators. For instance, Kneen et al. employed the GFP mutant S65T/F64L to determine the pH of the cytoplasm of CHO and LLC-PK1 cell lines (Kneen et al., *Biophys. J.* 74:1591–1599, 1998). Since GFP is genetically encoded, it can be specifically targeted to various subcellular compartments, which is a task not possible with small molecule fluorescent dyes (Llopis et al., *Proc. Natl. Acad. Sci. USA* 95:6803–6808, 1998). Therefore, Llopis and coworkers used the GFP variant S65G/S72A/T302Y/H231L, which has an increased $pK_a$, to measure the alkaline pH of mitochondria, golgi, and the cytosol of HeLa cells and rat neonatal cardiomyocytes (Llopis et al., 1998). These reports were the first to show that GFP variants could be used as biosensors and not just simple fluorescent markers. However, more recently GFP has been shown to be sensitive to halide ions and through a fusion with calmodulin, GFP's fluorescence can also vary in response to calcium ion concentration (Wachter et al., *Curr. Biol.* 9:R628–R629, 1999; Miyawaki et al., *Proc. Natl. Acad Sci. USA* 96:2135–2140, 1999).

Oxidation-reduction (redox) processes are very important in living organisms. The formation of disulfide bonds during protein folding relies upon a well maintained redox buffering system of glutathione and oxidized glutathione (Carothers et al., *Arch. Biochem. Biophys.* 268:409–425, 1989). There also exists a thioredoxin-like family of enzymes that catalyze the formation and isomerization of disulfide bonds in proteins (Debarbieux and Beckwith, *Cell* 99:117–119, 1999). In addition, redox signaling during apoptosis has been implicated in activating mitochondrial permeability transition, leading to cytochrome c release (Hall, *Eur. J. Clin. Invest.* 29:238–245, 1999). Redox changes in the form of cellular oxidation have also been suggested to be a final step in the apoptotic process leading to degradation of apoptotic bodies (Cai and Jones, *J. Bioenerg. Biomemb.* 31:327–334, 1999). Given the importance of in vivo processes such as protein folding and apoptosis that are dependant upon redox status, a non-invasive, convenient method for studying redox changes within living cells is needed.

Current methods of determining in vivo redox status have many limitations. Many present techniques require cells to be harvested before their contents can be analyzed. This type of procedure is not only very invasive but is also not a very accurate measure of the in vivo state of the cells. Moreover, it would be impossible with this technique to monitor redox changes within the same cell over a period of time. Recently, Keese et al., (Keese et al., *FEBS Lett.* 447:135–138, 1999) have developed an indicator of redox state in which glutathione reductase crystals were microinjected into the cytosol of human fibroblasts, and by detecting a color change of the crystals, they were able to determine the redox potential of the cytosol to be more reducing than –0.270 V. While this method may allow redox determination within single living cells, the cumbersome nature of the technique is still a major drawback. The most reasonable protocol for determining redox status is probably still that of Hwang et al. (Hwang et al., *Science* 257:1496–1502, 1992). They employed the tetrapeptide N-Acetyl-Asn-Tyr-Thr-Cys-$NH_2$ to measure the ratio of thiol to disulfide in the cytosol and secretory pathway of cultured cells. They concluded that the cytosol is more reducing than the secretory pathway with an approximate redox potential of –0.221 to –0236 V for the cytosol compared to –0.170 to –0.185 V for the secretory pathway. However, is method still required harvesting of the cells and like all the other methods, it is very labor intensive. Moreover, this technique determined redox potentials based only upon the ratio of reduced glutathione (GSH) to oxidized glutathione (GSSG), potentially ignoring other redox buffering components.

SUMMARY OF THE DISCLOSURE

To overcome disadvantages of available methods for determining redox status in cells, GFP mutants (also referred to as redox sensitive GFP (rosGFP) variants) have been designed and are described herein, which can detect or "sense" changes in oxidation-reduction potentials. The rosGFP variants have been engineered to have two cysteine amino acids near the chromophore and within disulfide bonding distance of each other.

To overcome disadvantages of available methods for determining redox status in cells, GFP mutants (also referred to as redox sensitive GFP (rosGFP) variants) have been designed and are described herein, which can detect or "sense" changes in oxidation-reduction potentials. The rosGFP variants have been engineering to have two cysteine amino acids near the chromophore and within disulfide bonding distance of each other.

Examples of the provided GFP variants have ratiometric dual-excitation fluorescent properties as a function of redox state, with apparent redox potentials of −0.272 to −0.299 V.

Specific embodiments include rosGFP mutants that differ from wild-type GFP in that they comprise at least the following amino acid substitutions:

(a) S147C/Q204C
(b) S65T/S147C/Q204C
(c) N149C/S202C
(d) S65T/N149C/S202C
(e) S147C/N149C/S202C/Q204C
(f) S65T/S147C/N149C/S202C/Q204C

The rosGFP mutants that include the S65T substitution are sensitive to pH as well as redox status. Particular provided mutation proteins include those referred to herein as rosGFP1, rosGFP2, rosGFP3, rosGFP4, rosGFP5, and rosGFP6.

Also provided are nucleic acid molecules encoding rosGFPs, including the specific listed rosGFPs. Optionally, these nucleic acid molecules can be functionally linked to expression control sequence(s) (such as a promoter), and/or integrated into a vector. Nucleic acid molecules encoding a rosGFP can be used to transform host cells (such as bacterial, plant, or animal cells); such transformed cells are also provided.

The disclosure also provides methods of using rosGFPs to analyze the redox status of a cell, or a subcellular compartment within a cell. In certain embodiments, both the redox status and pH of the cell (or subcellular compartment or other environment) are monitored concurrently.

BRIEF DESCRIPTION OF THE FIGURES

The patent or application file contains at least one drawing executed in color. Copies of this patent or patent application publication with color drawing(s) will be provided by the U.S. Patent and Trademark Office upon request and payment of the necessary fee.

SEQUENCE LISTING

Figure 1:
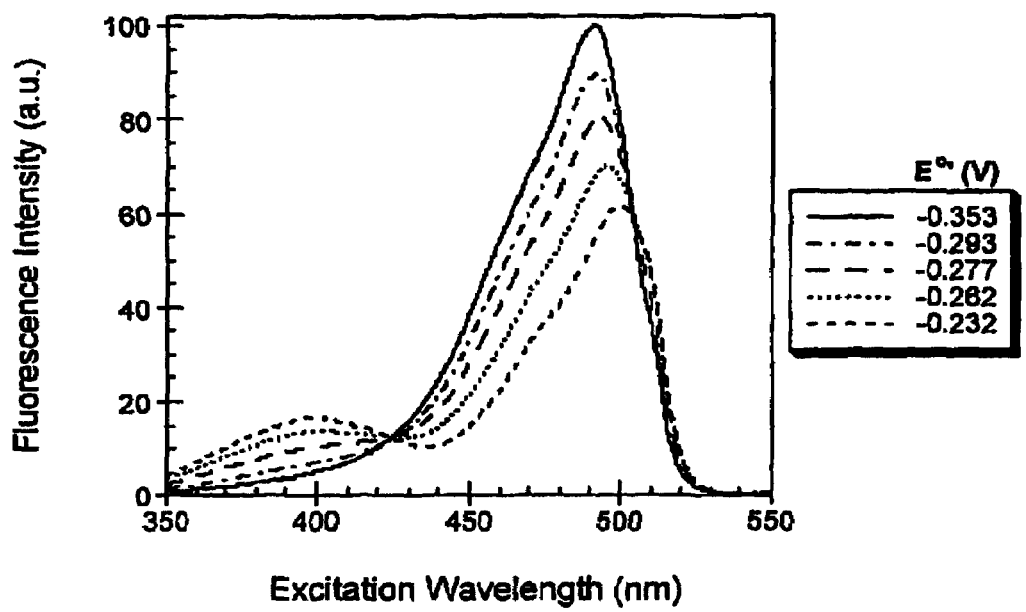
FIG. 1 is a fluorescence spectra graph, which shows how the fluorescence of rosGFP2 varies in response to changes in redox potential. The spectra show two excitation peaks, one near 400 nm and the other at about 490 nm, with a clear isosbestic point separating them.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary stand is understood as included by any reference to the displayed strand. In the accompanying sequence listing:

SEQ ID NO: 1 shows the amino acid sequence of wild-type GFP.
SEQ ID NO: 2 shows the nucleic acid and amino acid sequence of rosGFP2.
SEQ ID NO: 3 shows the amino acid sequence of rosGFP2.
SEQ ID NO: 4 shows the nucleic acid and amino acid sequence of rosGFP1.
SEQ ID NO: 5 shows the amino acid sequence of rosGFP1.
SEQ ID NO: 6 shows the nucleic acid and amino acid sequence of rosGFP4.
SEQ ID NO: 7 shows the amino acid sequence of rosGFP4.
SEQ ID NO: 8 shows the nucleic acid and amino acid sequence of rosGFP3.
SEQ ID NO: 9 shows the amino acid sequence of rosGFP3.
SEQ ID NO: 10 shows the nucleic acid and amino acid sequence of rosGFP6.
SEQ ID NO: 11 shows the amino acid sequence of rosGFP6.
SEQ ID NO: 12 shows the nucleic acid and amino acid sequence of rosGFP5.
SEQ ID NO: 13 shows the amino acid sequence of rosGFP5.
SEQ ID NO: 14 shows the amino acid sequence of a tetrapeptide used to measure the ratio of thiol to disulfide in the cytosol and secretory pathway of cultured cells.
SEQ ID NO: 15 shows the amino acid sequence of a nuclear localization sequence.
SEQ ID NO: 16 shows the amino acid sequence of a mitochondrion localization sequence.
SEQ ID NO: 17 shows the amino acid sequence of an endoplasmic reticulum localization sequence.

DETAILED DESCRIPTION

I. Abbreviations

| GFP | green fluorescent protein |
| rosGFP | redox-sensitive GFP |
| wtGFP | wild-type GFP |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments, the following explanations of specific terms are provided:

Animal: Living multi-cellular vertebrate organisms, a category that includes, for example, mammals and birds.

The term mammal includes both human and non-human mammals. Similarly, the term "subject" includes both human and veterinary subjects.

Antibody: A polypeptide substantially encoded by an immunoglobulin gene or imunoglobulin genes, or fragments thereof, which specifically binds and recognizes an analyte (antigen). Immunoglobulin genes include the kappa, lambda, alpha, gamma, delta, epsilon and mu constant region genes, as well as the myriad immunoglobulin variable region genes.

Antibodies exist, e.g., as intact immunoglobulins or as a number of well-characterized fragments produced by digestion with various peptidases. For instance, FAbs, Fvs, and single-chain Fvs (SCFvs) that bind to GFP would be GFP-specific binding agents. Antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')2, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. The term "antibody," as used herein, also includes antibody fragments either produced by the modification of whole antibodies or those synthesized de novo using recombinant DNA methodologies.

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells.

Conservative variations: Variants of a particular nucleic acid sequence, which encode identical or essentially identical amino acid sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified within a protein encoding sequence, the codon can be altered to any of the corresponding codons described without altering the encoded protein. Such nucleic acid variations are "silent variations," which are one species of conservative variations. Each nucleic acid sequence herein that encodes a polypeptide also describes every possible silent variation. The genetic code is shown in Table 1.

TABLE 1

| First position | Second position | | | | Third position |
|---|---|---|---|---|---|
| (5' end) | U | C | A | G | (3' end) |
| U | Phe | Ser | Tyr | Cys | U |
| | Phe | Ser | Tyr | Cys | C |

TABLE 1-continued

| First position | Second position | | | | Third position |
|---|---|---|---|---|---|
| (5' end) | U | C | A | G | (3' end) |
| | Leu | Ser | Stop | Stop | A |
| | Leu | Ser | Stop | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

One of skill will recognize that each codon in a nucleic acid (except AUG, which is ordinarily the only codon for methionine) can be modified to yield a functionally identical molecule by standard techniques. Accordingly, each "silent variation" of a nucleic acid that encodes a polypeptide is implicit in each described sequence.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valime (V); and
6) Phenylalanine (F), Tyrosine (Y), Tryptophan (W).

Not all residue positions within a protein will tolerate an otherwise "conservative" substitution. For instance, if an amino acid residue is essential for a function of the protein, even an otherwise conservative substitution may disrupt that activity. By way of example, in a GFP the residues that compose the chromophore do not generally tolerate amino acid substitutions.

Epitope tags: Short stretches of amino acids to which a specific antibody can be raised, which in some embodiments allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("western"), and affinity chromatography. Examples of useful epitope tags include FLAG, T7, HA (hemagglutinin) and myc.

Expression control sequence: This phrase refers to nucleotide sequences that regulate the expression of a nucleotide sequence to which they are operatively linked. Expression control sequences are "operatively linked" to a nucleotide sequence when the expression control sequences control and regulate the transcription and, as appropriate, translation of the nucleotide sequence. Thus, expression control sequence(s) can include promoters, enhancers, transcription terminators, a start codon (i.e., ATG) in front of a protein-encoding sequence, intron splicing signals, and stop codons.

Fluorescent property: A characteristic of a fluorescent molecule. Examples of fluorescent properties include the molar extinction coefficient at an appropriate excitation wavelength, the fluorescence quantum efficiency, the shape of the excitation spectrum or emission spectrum (the "fluorescence spectrum", the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild-type *Aequorea* GFP and the mutant form is useful. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing," respectively) for a particular molecule are advantageous. The ratioing process provides an internal reference and cancels out variations, for instance in the absolute brightness of the excitation source, the sensitivity of the detector, and light scattering or quenching by the sample.

Fusion protein: Proteins that have two (or more) parts fused together, which are not found joined together in nature. In general, the two domains are genetically fused together, in that nucleic acid molecules that encode each protein domain are functionally linked together, for instance by a linker oligonucleotide, thereby producing a single fusion-encoding nucleic acid molecule. The translated product of such a fusion-encoding nucleic acid molecule is the fusion protein.

Green fluorescent protein (GFP): GFP is a 238 amino acid, spontaneously fluorescent protein, originally isolated from the Pacific Northwest jellyfish *Aequorea victoria*. The amino acid sequence of wtGFP is shown in SEQ ID NO: 1. Tis protein has become an extremely popular tool in molecular and call biology (for reviews: Tsien, *Annu. Rev. Biochem.* 67:509–544, 1998; Remington, In *Bioluminescence and chemiluminescence* (eds. T. O. Baldwin and M. M. Sigler), pp. 195–211, 2000, Academic, San Diego, Calif.). Originally GFP was used as a passive indicator of gene expression and protein localization. More recently, GFP has taken on the role of an active indicator of such things as intracellular $H^+$, $Ca^{2+}$, and halide ion concentrations (Kneen et al., *Biophys. J.* 74:1591–1599, 1998; Llopis et al., *Proc. Natl. Acad. Sci. USA* 95:6803–6808, 1998; Baird et al., *Proc. Natl. Acad. Sci. USA* 96:11241–11246, 1999; Jayaraman et al., *J. Biol. Chem.* 275:6047–6050, 2000).

In addition to GFP being highly fluorescent, protease resistant, and very stable throughout a wide range of pH and solvent conditions, it also has the advantage of being functional as a single protein encoded by a single gene. These traits result in a biological probe molecule that can be expressed in nearly all organisms. It also can be targeted to subcellular organelles by a host cell, for instance through the inclusion of a targeting sequence on the construction from which it is expressed. GFP is a non-invasive indicator, which allows for experiments to be conducted and monitored in a single cell over a period of time.

GFPs as discussed herein (including rosGFPs) can be expressed as fusion proteins. The GFP protein can be functionally fused to, for instance, a tag (such as an epitope tag), a targeting molecule (such as a targeting peptide), or a protein (or fragment thereof) that provides an additional function, such as a biochemical, biological, or localization function. The construction and production of fusion proteins is well known to one of ordinary skill in the art.

A "mutant" GFP is a green fluorescent protein (or nucleic acid encoding such) that has at least one residue that is different from (mutated from) the wtGFP. Mutations include, for instance, conservative or non-conservative amino acid substitutions, silent mutations (wherein the nucleic acid sequence is different from wild-type at a particular residue, but the amino acid sequence is not), insertions (including fusion proteins), and deletions. Myriad mutant GFPs are known, including for instance those disclosed in the following patent documents: U.S. Pat. Nos. 5,804,387; 6,090,919; 6,096,865; 6,054,321; 5,625,049; 5,874,304; 5,777,078; 5,968,750; 6,020,192; and 6,146,826; and published international patent application WO 99/64592.

Specific examples of mutant GFPs include proteins in which the fluorescence spectrum of the mutant is responsive to an environmental variable, such as temperature, proton concentration (pH), salt concentration, and redox status. Particular mutant GFPs as provided herein are sensitive to redox status, and others are responsive to both redox status and pH. A fluorescence spectrum is "responsive" to an environmental variable if the spectrum changes with changes in that variable.

Immunoassay: An assay that utilizes an antibody to specifically bind an analyte. The immunoassay is characterized by the use of specific binding properties of a particular antibody to isolate, target, detect, and/or quantify the analyte, or alternately using a particularly analyte (e.g., an antigen) to isolate, target, detect, and/or quantify the antibody.

In vitro amplification: Techniques that increases the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification may be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles.

Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A composition detectable by spectroscopic, photochemical, biochemical, immunochemical, or chemical means. For example, useful labels include $^{32}P$ (or other radio-isotope), fluorescent dyes, fluorescent proteins, electron-dense reagents, enzymes (e.g., for use in an ELISA), biotin, dioxigenin, or haptens and proteins or peptides for which antisera or monoclonal antibodies are available. A label often generates a measurable signal, such as radioactivity, fluorescent light or enzyme activity, which can be used to detect and/or quantitate the amount of labeled molecule.

Nucleic acid: A deoxyribonucleotide or ribonucleotide polymer in either single- or double-stranded form. Unless otherwise limited, this term encompasses known analogs of natural nucleotides that can function in a similar manner as naturally occurring nucleotides. When a nucleic acid molecule is represented herein by a DNA sequence, the corresponding RNA molecules are likewise understood, in which "U" replaces "T."

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10–25 bases, such as 12, 15 or 20 bases.

Open reading frame: A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. Similarly, two peptide or polypeptide sequences are considered to be operably linked if they are linked to each other in such a way that they function in the intended manner.

Polypeptide or Protein: A polymer of amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence (which encodes the protein) from a recombinant DNA molecule.

Preferred mammalian codon(s): The subset of codons from among the set of all possible codons encoding an amino acid that are most frequently used in proteins expressed in mammalian cells. Table 2 summarizes the preferred mammalian codons for each amino acid:

TABLE 2

| Amino Acid | Preferred codons* |
|---|---|
| Gly | GGC, GGG |
| Glu | GAG |
| Asp | GAC |
| Val | GUG, GUC |
| Ala | GCC, GCU |
| Ser | AGC, UCC |
| Lys | AAG |
| Asn | AAC |
| Met | AUG |
| Ile | AUC |
| Thr | ACC |
| Trp | UGG |
| Cys | UGC |
| Tyr | UAU, UAC |
| Leu | CUG |
| Phe | UUC |
| Arg | CGC, AGG, AGA |
| Gln | CAG |
| His | CAC |
| Pro | CCC |

Primers: Primers are short nucleic acid molecules, for instance DNA oligonucleotides 10 nucleotides or more in length. Longer DNA oligonucleotides May be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length.

Probes: A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., Sambrook et al. (In *Molecular Cloning: A Laboratory Manual*, CSHL, New York:, 1989) and Ausubel et al. (In *Current Protocols in Molecular Biology*, John Wiley & Sons, New York, 1998).

Promoter: A promoter is an ordered set of nucleic acid control sequences that direct transcription of a nucleic acid. A promoter includes necessary nucleic acid sequences near the start site of transcription, such as, in the case of a polymerase II type promoter, a TATA element. A promoter also optionally includes distal enhancer or repressor elements that can be located as much as several thousand base pairs from the start site of transcription.

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Recombinant host cell: A cell (such as a bacterial, plant, or animal cell) that comprises a recombinant nucleic acid molecule. Thus, for example, recombinant host cells can express genes and/or proteins that are not found within the native (non-recombinant) form of the cell.

Redox status: A measurement of the oxidation-reduction (redox) potential of an environment, for instance the environment within a cell or a subcellular compartment.

Fundamentally, redox reactions are a family of reactions that are concerned with the transfer of electrons between species. Oxidation represents a loss of electrons, reduction a gain of electrons. Oxidation-reduction reactions always occur together, and the electrons gained by the molecule that is reduced must balance those given up by the substance that is oxidized. The oxidation-reduction potential (or redox status) of a solution is a measurement of the oxidation or reduction force of the solution, and is indicative of the oxidation or reduction ability.

Redox status of any solution can be measured. For instance, the redox status of the solution within a cell (i.e., the cytosol) can be analyzed using the provided rosGFPs. Similarly, the redox status of the solution within a subcellular organelle (such as the nucleus, mitochondria, plastid, vacuole, secretory pathway compartment and so forth) can be analyzed.

Stringent conditions: A set of temperature and ionic conditions used in a nucleic acid hybridization. Stringent conditions are sequence dependent and are different under different environmental parameters. Generally, stringent conditions are selected to be about 5° C. to 20° C. lower than the thermal melting point ($T_m$) for the specific target sequence. The $T_m$ is the temperature (under defined ionic strength and pH) at which 50% of the target sequence hybridizes to a perfectly matched (100% identical) probe molecule.

Substantially identical/similar: An amino acid sequence or a nucleotide sequence is substantially identical (or substantially similar) to a reference sequence if the amino acid sequence or nucleotide sequence has at least 80% sequence identity with the reference sequence over a given window of comparison. Thus, substantially similar sequences include those having, for example, at least 85% sequence identity, at least 90% sequence identity, at least 95% sequence identity or at least 99% sequence identity. Two sequences that are 100% identical to each other are, of course, also substantially identical.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Comprises means includes. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples am illustrative only and not intended to be limiting.

III. Redox-Sensitive Green Fluorescent Proteins

Many fundamental biological processes rely upon a properly maintained intracellular redox environment (Cuozzo and Kaiser, *Nat. Cell Biol.* 1:130–135, 1999; Debarbieux and Beckwith, *Cell* 99:117–119, 1999; Hall, *Eur. J. Clin. Invest.* 29:238–245, 1999; Cai and Jones, *J. Bioenerg. Biomemb.* 31:327–334, 1999). Moreover, reactive oxygen species like $O_2$—$^-$; HO—, or $H_2O_2$, arise in cells by a variety of processes including light, radiation, or the respiratory chain. These radical species present major threats to organisms by damaging DNA, membranes, or other cellular components.

The importance of redox status to biological process might imply that researchers have numerous well-established techniques for monitoring redox potentials in vivo. However, this is not the case. Current redox-sensing methods are invasive, require large sample sizes, are labor intensive, and do not allow for real-time determinations on living cells.

This disclosure describes a new class of GFP variants (rosGFPs) that display ratiometric excitation properties as a function of redox potential. rosGFP biosensors allow for real-time measurements of redox status on small groups of cells, individual cells, or even within certain cellular organelles. As a result of being genetically encoded, these molecules are non-invasive, and their fluorescence characteristics they are easy to use as sensing molecules.

To create a redox sensor that overcomes many of the drawbacks of other methods of in vivo redox status determination, site-directed mutagenesis was carried out on the green fluorescent protein (GFP). By mutating residues near the chromophore in GFP to cysteines, novel redox-sensitive GFPs (rosGFPs) were constructed. They display ratiometric dual-excitation fluorescent properties as a function of redox state, with apparent redox potentials of –0.272 to –0.299 V.

Unexpectedly, these rosGFPs also exhibited ratiometric dual-emission properties in response to pH changes, providing the unique possibility to simultaneously monitor redox potential and pH changes with the same probe. T65S reversion leads to pH-independent redox sensors with altered redox potentials and large UV excitation peaks, which can be used to overcome background levels of cellular autofluorescence.

Crystal structure analyses of an oxidized and reduced rosGFP to 1.9 and 2.0 Å, respectively, indicate that changes in the structure on reduction or oxidation of the disulfide bridge could account for the observed spectral changes.

As shown herein using cultured HeLa cells, rosGFPs can reversibly respond to exogenous redox stimuli and have redox potentials near that of mitochondria, with the apparent redox potential of mitochondria estimated to more reducing than about −0.30 V. The apparent redox potential of the cytosol also was found to be more reducing than −0.30 V.

One example redox sensitive GFP mutant (rosGFP2) differs from wild-type GFP in that it contains the following amino acid residue mutations: C48S/S65T/Q80R/S147C/Q204C (SEQ ID NOs: 2 and 3). FIG. 1 illustrates how the fluorescence of rosGFP2 varies in response to changes in redox potential. The spectra show two excitation peaks, one near 400 nm and the other at about 490 nm, with a clear isosbestic point separating them. These dual excitation peaks respond in opposite directions to redox potential, making this indicator ratiometric for redox potential. Ratiometric indicators are known to reduce or eliminate distortions of data caused by photobleaching, indicator concentration, variable cell thickness, illumination stability, excitation pathlength, and non-uniform indicator distribution within cells or between groups of cells (Grynkiewicz et al., *J. Biol. Chem.* 260:3440–3450, 1985).

Figure 2:
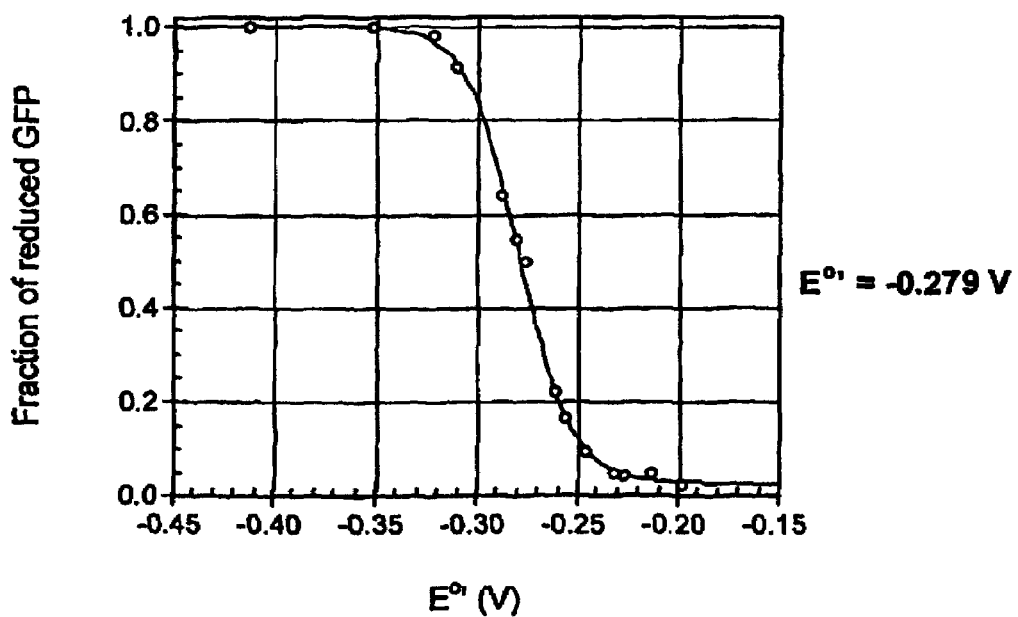
FIG. 2 shows the titration of rosGFP2 with dithiothreitol. The apparent redox potential is −0.279 volts.
Figure 3:
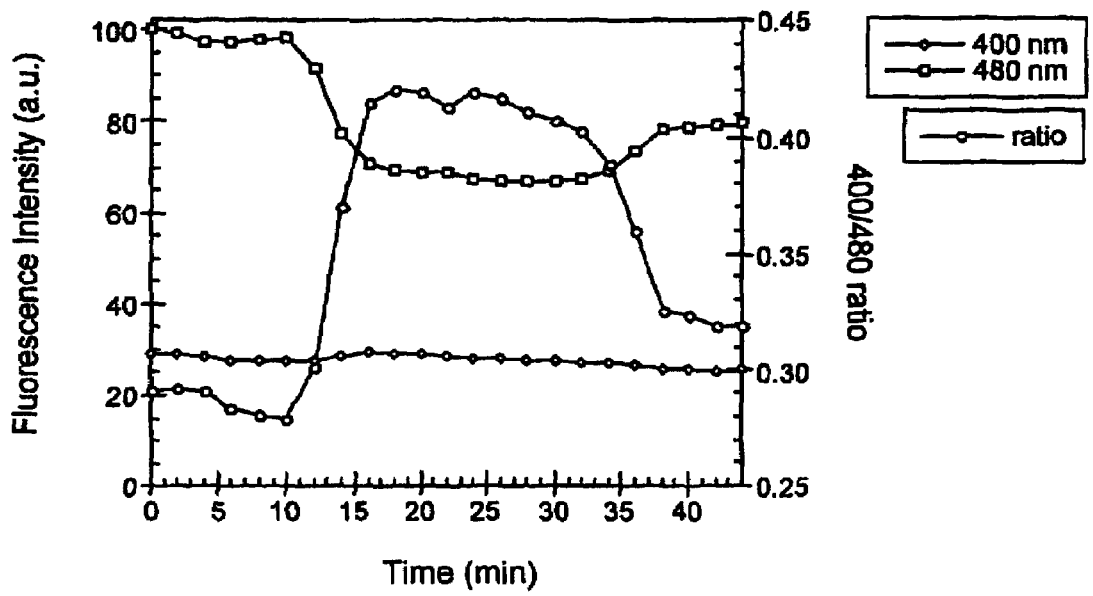
FIG. 3 is a graph showing the in vivo redox changes in fluorescence intensity of rosGFP2, in response to the addition of vitamin in $K_3$. After 30 total minutes, the addition of dithiothreitol elicits the opposite response as indicated by the reduced ratio.

By monitoring the chromophore fluorescence at the 490 nm excitation peak as a function of redox potential, the apparent redox potential of rosGFP2 was found FIG. 2 shows the titration of rosGFP2 with dithiothreitol. From this plot the apparent redox potential is −0.279 volts. To demonstrate that the redox-sensitive probe responds to in vivo redox changes, it was targeted to the mitochondria of HeLa cells. As seen in FIG. 3, the starting ratio of the 400 to 490 nm peak in mitochondria is around 0.28. After the addition of the redox-cycling agent vitamin $K_3$, the ratio dramatically increases to about 0.42. This increase in the ratio is indicative of an oxidation event that is to be expected according to the reaction catalyzed by vitamin $K_3$ (Suttie, *Annu. Rev. Biochem.* 54:459–477, 1985). After 30 total minutes, the addition of dithiothreitol elicits the opposite response as indicated by the smaller ratio.

Characteristics of several redox-sensitive GFP mutants are summarized in Table 3.

Properties of rosGFPs

Examples of redox-sensitive GFPs described herein have many desirable qualities. In addition to being genetically encoded fluorescent indicators, they are ratiometric. This ratiometric behavior has the advantage of reducing or eliminating distortions of data caused by photobleaching, indicator concentration, variable cell thickness, illumination stability, excitation path length, and non-uniform indicator distribution within cells or between groups of cells (Grynkiewicz et al., *J. Biol. Chem.* 260:3440–3448, 1985; Whitaker et al., *Anal. Biochem.* 194:330–344, 1991). In addition, a ratio of excitation wavelengths greatly minimizes the contribution of pH artifacts to the fluorescent signal over a pH range from 6 to 8.5. Similarly, a ratio of emission wavelengths can result in pH monitoring without artifacts introduced by the redox state of the biosensor.

The second-generation rosGFPs, with more closely matched excitation peak amplitudes, may aid in fluorescence microscopy experiments by allowing the same camera/detector settings to capture both images that constitute the ratio. Furthermore, second-generation rosGFPs have a larger 400 nm fluorescence amplitude, which is desirable for detection of the rosGFP probe over background levels of cellular autofluorescence.

Accuracy of Standard Redox Potentials

The main problem in the determination of redox potentials is that $E_o$ values cannot be measured directly, but rather are calculated from the known $E_o$ of another redox couple, equilibrated with the redox couple of unknown $E_o$. The standard redox potential can thus vary over a large range depending on experimental conditions and the choice of redox couple.

In this disclosure, the value of −0.323 V for the dithiothreitol couple was chosen, because it has been very accurately determined in 0.05–0.02 M phosphate buffer at pH 7.0 and 30.0°+/−0.5° C. using the lipoamide-lipoamide dehydrogenase couple (Szajewski and Whitesides, *J. Am. Chem. Soc.* 102:2011–2026, 1980). Because redox potentials are pH and temperature dependent, all redox equilibria were measured at the same pH (7.0) and temperature (30° C.) as was used to evaluate the standard redox potential of the dithiothreitol couple. Another reason to use the value of −0.323 V for the dithiothreitol couple is that the standard potentials of other commonly used thiol reagents (including the GSH-GSSG couple) have been determined under identical conditions (Szajewski and Whitesides, *J. Am. Chem. Soc.* 102:2011–2026, 1980). This will allow for the direct

TABLE 3

| Mutant name | Substitutions | Excitation Peaks | Redox Potential* |
|---|---|---|---|
| rosGFP2 | C48S/S65T/S147C/Q204C | 400 nm | −0.272 |
|  | (SEQ ID NOs: 2 and 3) | 490 nm |  |
| rosGFP1 | C48S/S147C/Q204C | 397 nm | −0.288 |
|  | (SEQ ID NOs: 4 and 5) | 477 nm |  |
| rosGFP4 | C48S/S65T/N149C/S202C | 400 nm | −0.286 |
|  | (SEQ ID NOs: 6 and 7) | 490 nm |  |
| rosGFP3 | C48S/N149C/S202C | 392 nm | −0.299 |
|  | (SEQ ID NOs: 8 and 9) | 475 nm |  |
| rosGFP6 | C48S/S65T/S147C/N149C/S202C/Q204C | 398 nm | −0.280 |
|  | (SEQ ID NOs: 10 and 11) | 490 nm |  |
| rosGFP5 | C48S/S147C/N149C/S202C/Q204C | 395 nm | −0.296 |
|  | (SEQ ID NOs: 12 and 13) | 475 nm |  |

*volts comparison of redox potentials determined by use of rosG-FPs to those determined by other methods, provided the experimental conditions are reproduced.

For the $DTT_{red}$-$DTT_{ox}$ couple, the standard potential throughout literature is well accepted to be about −0.330 V at near biochemist's standard state of pH 7 and 25° C. However, such agreement is not always the norm. In the case of the glutathione redox couple, very different values for the standard redox potential have been reported. The published values deviate from a somewhat oxidizing value of −0.205 V to a more reducing value of −0.250 V (Szajewski and Whitesides, *J. Am. Chem. Soc.* 102:2011–2026, 1980; Rost and Rapoport, *Nature* 201:185, 1964; Torchinsky, *Sulfur in proteins*. Pergamon Press Ltd., 1981, New York, N.Y.). The 45 mV difference in literature values might be problematic when trying to compare redox potentials of rosGFPs to previously determined estimates of the redox potential inside cells.

Even with the large discrepancy in the standard potential of GSH-GSSG, results reported herein indicate that in vivo redox potentials may be more reducing than previous estimates. Hwang et al., using the tetrapeptide N-Acetyl-Asn-Tyr-Thr-Cys-$NH_2$ (SEQ ID NO: 14) to measure the ratio of thiol to disulfide in the cytosol and secretory pathway of cultured cells, concluded that the cytosol is more reducing than the secretory pathway with an approximate redox potential of −0.221 to −0.236 V versus −0.170 to −0.185 V, respectively (Hwang et al., *Science* 257:1496–1502, 1992). In addition, based on prior determinations of the concentration and ratio of GSH to GSSG in mitochondria, the redox potential of this compartment is calculated to be −0.210 to −0.230 V. However, Keese et al. recently developed an indicator of redox state in which they transfer glutathione reductase crystals into the cytosol of living cells and then detect a color change in the crystals (Keese et al., *FEBS Lett.* 447:135–138, 1999). Using that method, Keese et al. determined the redox potential of the cytosol of human fibroblasts to be more reducing than −0.270 V at pH 7.4 and 37° C. That result is in agreement with the estimate reported herein of the cytosolic redox potential for HeLa cells being more negative than −0.330 V.

IV. Construction of rosGFPs

The examples below provide specific methods for producing certain embodiment rosGFPs. More generally, in light of the disclosure herein that disulfide bonding pairs can be incorporated into GFP to produce redox-sensitive GEP mutants, it will be understood to one of ordinary skill in the art that many different methods could be used to make rosGFPs.

A. GFP Nucleic Acids and Site-directed Mutations

DNA encoding wtGFP is available commercially, for example from CLONTECH (Palo Alto, Calif.). Methods of producing mutants containing a predetermined nucleotide sequence are well known to those of ordinary skill in the art. Two widely used methods are Kunkel mutagenesis and PCR mutagenesis. A detailed description of the two techniques can be found in *Current Protocols in Molecular Biology*, Wiley Interscience, 1987, Sections 8.1 and 8.5 respectively. See also Kunkel, *Proc. Acad. Nat. Sci. USA* 82:488–492, 1985; and Saiki et al., *Science* 239:487–491, 1988.

It is also possible to synthesize mutant GFPs and DNA encoding for mutant GFPs directly, by synthetic methods well known in the art. The mutant sequences can be expressed in a variety of systems, including bacterial, yeast, plant and mammalian cells. DNA encoding the mutant GFP is inserted in an expression vector and transformed into cells of interest. The sequence encoding for GFP is inserted in the vector in the correct reading frame near a strong promoter, and the expression of GFP is induced. Vectors suitable for specific expression systems are well known in the art, and are widely available commercially. Vectors having codons opted for expression in a variety of systems, including yeast and mammalian cells, are also available. For a description of silent nucleotide sequence mutations optimized for mammalian expression, see for example Haas et al. (*Curr. Biol.* 6:315–324, 1996).

B. Expression of rosGFPs

One skilled in the art will understand that there are myriad ways to express a recombinant protein such that it can subsequently be purified. In general, an expression vector carrying the nucleic acid sequence that encodes the desired protein will be transformed into a microorganism for expression. Such microorganisms can be prokaryotic (bacteria) or eukaryotic (eg., yeast). One appropriate species of bacteria is *Escherichia coli* (*E. coli*), which has been used extensively as a laboratory experimental expression system. A eukaryotic expression system will be preferred where the protein of interest (or a domain within a fusion protein of interest) requires eukaryote-specific post-translational modifications such as glycosylation. Also, protein can be expressed using a viral (e.g., vaccinia) based expression system. Protein can also be expressed in animal cell tissue culture, and such a system will be appropriate where animal-specific protein modifications are desirable or required in the recombinant protein.

The expression vector can include a sequence encoding a targeting peptide, positioned in such a way as to be fused to the coding sequence of the rosGFP. Targeting domains may allow the fusion protein to be targeted to specific extracellular locations, or simply to be secreted from the cell, and may be removed during or soon after synthesis of the fusion protein. In addition, multiple targeting peptides can be included in a single fusion, for instance a peptide/domain that directs the fusion protein to be secreted, and another peptide/domain that directs the secreted protein to a target (cell, tissue, organ, etc.). Various appropriate prokaryotic and eukaryotic targeting peptides, and nucleic acid molecules encoding such, are known to one of ordinary skill in the art. Through the use of a eukaryotic secretion-type signal sequence, a rosGFP fusion protein can be expressed in a transgenic animal (for instance a cow, pig, or sheep) in such a manner that the fusion protein is secreted into the milk of the animal. Targeting protein portions also may be used to ensure that a transgenically expressed fusion protein is secreted into the circulatory system of the transgenic animal, thereby permitting the fusion protein to be transported to a target (cell, tissue, organ, etc.).

Optional localization peptide sequences may be, for instance, a nuclear localization sequence, an endoplasmic reticulum localization sequence, a peroxisome localization sequence, a mitochondrial localization sequence, or a localized protein. Localization sequences can be targeting sequences which are described, for example, in "*Protein Targeting*," chapter 35 of Stryer, *Biochemistry* (4th ed.). W. H. Freeman, 1995. The localization sequence can also be a localized protein (or domain thereof). Some localization sequences include the following non-limiting examples (Table 4):

TABLE 4

| Subcellular location | Localization sequence(s) |
|---|---|
| nucleus | KKKRK |
| mitochondrion | MLRTSSLFTRRVQPSLFRNILRLQST-* |
| endoplasmic reticulum | KDEL** (providing retention in the ER) when used with a signal sequence* |
| peroxisome | SKF** |
| prenylation or insertion into plasma membrane | CaaX, CC, CXC, or CCXX** |
| cytoplasmic side of plasma membrane | fusion to SNAP-25 |
| Golgi | fusion to furin |

*amino terminal
**carboxy terminal

Vectors suitable for stable transformation of culturable cells are also well known. Typically, such vectors include a multiple-cloning site suitable for inserting a cloned nucleic acid molecule, such that it will be under the transcriptional control of 5' and 3' regulatory sequences. In addition, transformation vectors include one or more selectable markers; for bacterial transformation this is often an antibiotic resistance gene. Such transformation vectors typically also contain a promoter regulatory region (e.g., a regulatory region controlling inducible or constitutive expression), a transcription initiation start site, a ribosome binding site, an RNA processing signal, and a transcription termination site, each functionally arranged in relation to the multiple-cloning site. For production of large amounts of recombinant proteins, an inducible promoter is preferred. This permits selective production of the recombinant protein, and allows both higher levels of production than constitutive promoters, and enables the production of recombinant proteins that may be toxic to the expressing cell if expressed constitutively.

In addition to these general guidelines, protein expression/purification kits are produced commercially. See, for instance, the QIAEXPRESS™ expression system from QIAGEN (Chatsworth, Calif.) and various expression systems provided by INVITROGEN (Carlsbad, Calif.).

C. Purification of rosGFPs

One skilled in the art will understand that there are myriad ways to purify recombinant polypeptides, and such typical methods of protein purification may be used to purify the disclosed rosGFPs. Such methods include, for instance, protein chromatographic methods including ion exchange, gel filtration, HPLC, monoclonal antibody affinity chromatography and isolation of insoluble protein inclusion bodies after over production. In addition, purification affinity-tags, for instance a six-histidine sequence, may be recombinantly fused to the protein and used to facilitate polypeptide purification (e.g., in addition to another functionalizing portion of the fusion, such as a targeting domain or another tag). A specific proteolytic site, for instance a thrombin-specific digestion site, can be engineered into the protein between the tag and the remainder of the fusion to facilitate removal of the tag after purification, if such removal is desired.

Commercially produced protein expression/purification kits provide tailored protocols for the purification of proteins made using each system. See, for instance, the QIAEXPRESS™ expression system from QIAGEN (Chatsworth, Calif.) and various expression systems provided by INVITROGEN (Carlsbad, Calif.). Where a commercial kit is employed to produce a rosGFP, the manufacturer's purification protocol is a preferred protocol for purification of that protein. For instance, proteins expressed with an amino-terminal hexa-histidine tag can be purified by binding to nickel-nitrilotriacetic acid (Ni-NTA) metal affinity chromatography matrix (The QIAexpressionist, QIAGEN, 1997).

D. Optional Modifications to rosGFPs

Optionally, redox-sensitive GFP variants/mutants can be "humanized" as described in U.S. Pat. No. 5,874,304, or can contain other mutations (such as substitutions) as dictated by the end-use of the protein.

Also, the mutant GFP proteins can be expressed as part of a fusion protein. The construction of fusion proteins from domains of known proteins, or from whole proteins or proteins and peptides, is well known. In general, a nucleic acid molecule that encodes the desired protein and/or peptide portions are joined using genetic engineering techniques to create a single, operably linked fusion oligonucleotide. Appropriate molecular biological techniques may be found in Sambrook et al. (1989). Examples of genetically engineered multi-domain proteins, including those joined by various linkers, and those containing peptide tags, can be found in the following patent documents:

U.S. Pat. No. 5,994,104 ("Interleukin-12 fusion protein");
U.S. Pat. No. 5,981,177 ("Protein fusion method and construction");
U.S. Pat. No. 5,914,254 ("Expression of fusion polypeptides transported out of the cytoplasm without leader sequences");
U.S. Pat. No. 5,856,456 ("Linker for linked fusion polypeptides");
U.S. Pat. No. 5,767,260 ("Antigen-binding fusion proteins");
U.S. Pat. No. 5,696,237 ("Recombinant antibody-toxin fusion protein");
U.S. Pat. No. 5,587,455 ("Cytotoxic agent against specific virus infection");
U.S. Pat. No. 4,851,341 ("Immunoaffinity purification system");
U.S. Pat. No. 4,703,004 ("Synthesis of protein with an identification peptide"); and
WO 98/36087 ("Immunological tolerance to HIV epitopes").

In particular, patent disclosures related to fusion proteins containing a GFP moiety include the following:

U.S. Pat. No. 6,180,343 ("Green fluorescent protein fusions with random peptides");
WO 99/54348 ("Rapidly degrading GFP-fusion proteins and methods of use");
WO 99/19470 ("GFP-annexin fusion proteins")
WO 98/14605 ("Renilla luciferase and green fluorescent protein fusion genes"); and
EP 949269 ("Biosensor protein").

V. Applications

With the provision of redox-sensitive GFP indicators, methods of monitoring redox changes in real time in a targeted environment, for instance in the mitochondria (or other subcellular compartment) of single living cells, are enabled.

Redox-sensitive GFPs mutant are useful in a wide variety of applications, including the monitoring of redox status of individual cells or subcellular compartments. Certain of the provided rosGFPs are also useful for monitoring pH concurrently with redox status, as explained herein.

Mutant GFPs as described herein are suitable for use as markers for transformation of mammalian cells. Often, a gene of therapeutic interest does not produce an easily distinguishable phenotype in cells expressing that gene.

Thus, such a therapeutic gene can be inserted into a vector that contains a marker gene. The therapeutic gene and the marker gene are placed in the vector under the control of a cellular or viral promoter, and introduced into mammalian cells of interest; subsequently, the transfected cells (the cells containing the vector) are selected according to the phenotype determined by the marker gene. The use of GFP for selection obviates the need to grow the mammalian cells of interest in the presence of drugs in order to select for the transfected cells. In addition, due to the redox-sensitive nature of the provided GFP mutants, the redox status of the transformed cells (or respective subcellular compartment(s)) can be directly measured. Cells transformed with a nucleic acid comprising a rosGFP can be sorted by FACS.

For the study of protein localization, fusion of a rosGFP mutant and a sequence encoding a cellular protein (or encoding a fragment, sub-domain, or domain of a protein), and subsequent expression of the fusion construct, results in a fluorescent fusion protein that is localized at the normal intracellular location of the protein encoded by the nucleic acid sequence of interest. Identifying the intracellular location of the mutant GFP thus identifies the intracellular location of the protein of interest. The use of such fusion proteins yields information on the normal cellular role of the protein encoded by the gene of interest, and provides direct measurement of the redox status (and in some embodiments, pH) of the intracellular environment to which it was targeted. Such an application using wtGFP is described in more detail, for example, in an article by Olson et al. (*J. Cell Biol.*, 130:639–650,1995).

Also provided are rosGFPs that are sensitive to pH, including for instance rosGFP2, 4, and 6. Dual sensor GFPs such as these can be used in any situation in which it is beneficial to monitor or measure both pH and redox status in an environment.

VI. Kits

Kits are provided that contain at least one rosGFP protein, or a nucleic acid molecule (e.g., a vector) that encodes such a protein, or both, in one or more contains. The provided kits may also include written instructions. The instructions can provide calibration curves or charts to compare with the determined (e.g., experimentally measured) values. Included are kits that can be used for diagnosis or prognosis of a disease or other condition associated with a change in the redox status of cell or sub-cellular compartment.

The invention is illustrated by the following non-limiting Examples.

EXAMPLES

Example 1

Selection and Design of Redox-Sensitive GFPs

In order to create redox-sensitive GFPs, two cysteine residues were introduced into GFP that would be within disulfide bonding distance of each other, near the chromophore, and on the surface of the protein. The cysteine residues bring about fluorescence changes based upon whether they are reduced or oxidized. In addition, by being on the surface of the protein, the cysteines are solvent accessible, which enables them to reversibly respond to redox changes in the surrounding environment.

After close examination of the crystal structure of the S65T variant of GFP, two borderline suitable sites for the introduction of a pair of cysteines were chosen. The first site chosen was positions 147 and 204, while the second site chosen was positions 149 and 202. All four amino acid side-chains at these positions pointed away from the protein's interior. The distance between the $C_\alpha$—$C_\alpha$ and $C_\beta$—$C_\beta$ positions for site one were 4.6 Å each, and for site two the distance between these positions were 4.8 and 5.9 Å, respectively. These distances did not agree with previous reports on ideal geometry for the introduction of disulfide bridges in proteins. In addition, neither of these site pairs were chosen by a disulfide bridge modeling program (Sowdhamini et al., *Protein Eng.* 3:95–103, 1989). There were, however, some indications that one or both of these pairs of cysteines might be able to form a disulfide bond. Such evidence came from the irregular "bulging" nature of the β-strand encompassing positions 147 and 149, which has previously been shown to move in response to substitution at position 148 (Wachter et al., *Structure* 6:1267–1277, 1998). Flexibility has been suggested to help ensure that a protein can both adjust to the perturbation due to replacements with cysteine residues as well as to allow the disulfide bridge to assume near-optimal geometry (Matsumura et al., *Proc. Natl. Acad. Sci. USA* 86:6562–6566, 1989). The 147/204 and 149/202 sites best fit the criteria.

Example 2

Construction and Expression of Redox Sensitive GFPs

Wild-type GFP contains two cysteine residues at positions 48 and 70. To avoid possible thiol/disulfide interchange reactions with the newly engineered cysteines, cysteine 48 and cysteine 70 were replaced with serine and alanine, respectively. Although the substitution C48S did not alter the properties of GFP, C70A appeared to be deleterious to obtaining soluble, fluorescent protein. Since position 70 is located within the interior of GFP and is in close proximity to the chromophore, it was deemed a mutation-sensitive position and was therefore left as a cysteine.

The C48S mutation was introduced into a histidine-tagged version of the S65T variant of GFP in the plasmid pRSET$_B$. This construct served as the template for introduction of the cysteines at sites one (S147C/Q204C) and two (N149C/S202C). All mutations were introduced via the QUICKCHANGE™ Site-Directed Mutagenesis Kit (Stratagene, La Jolla, Calif.), following the manufacturer's protocol. Mutations were verified by DNA sequencing of the entire GFP coding sequence.

Mutant protein was recombinantly expressed in *Escherichia coli*, strain JM109(DE3). Transformed bacteria were grown in four liters of S-LBH media at 37° C., stirred at 450 rpm, with 5 liters per minute air flow, and in the presence of 0.27 mM ampicillin. After the culture reached a density of approximately $OD_{595}$ equal to 0.8, then protein expression was induced by addition of isopropyl-β-D thiogalactopyranoside (IPTG) to a final concentration of 1 mM. At the same time the temperature of the culture was reduced to 16° C. and the culture allowed to grow for an addition 16 hours. Cells were then harvested by centrifugation at 4° C. in a Beckman KA-9.1000 rotor at 11,800×g for 10 minutes.

The bacterial cell pellet was resuspended in 100 mL of 50 mM HEPES (pH 7.9), 300 mM NaCl, 10% glycerol, and 0.1 mM phenylmethylsulfonyl fluoride (PMSF). The resuspended cells were sonicated for a total of five minutes, and the lysate clarified twice by centrifugation at 35,000×g in a Beckman JA-20 rotor at 4° C. for 20 minutes.

The resultant supernatant was loaded onto a pre-equilibrated nickel-nitrilotriacetic acid (Ni-NTA) metal-affinity column (Qiagen, Hilden, Germany). The equilibration and subsequent washing of the column was performed with washing buffer (50 mM HEPES (pH 7.9) and 300 mM NaCl). Proteins were eluted from the column by a step gradient of (1) washing buffer plus 20 mM imidazole to remove mostly unwanted proteins, and then (2) washing buffer plus 100 mM imidazole to elute the mutant GFP. To remove the amino-terminals histidine tag and as a filer purification step the eluted protein was incubated with 1/50 w/w γ-chymotrypsin at 22° C. for 22 hours. The protein preparation was finally buffer exchanged on a Sephadex® G-25 column. Characteristic yields of mutant GFP protein were in the range of 15 to 100 milligrams and with a purity greater than 95%.

Example 3

Disulfide-Bond Formation and Redox Sensitivity of rosGFPs

Samples of rosGFP2 and GFP S65T (control) were treated with 1 mM DTT or 1 μM $CuCl_2$ and incubated at room temperature for 3–4 hours, then 2 mM N-ethyl maleimide was added to prevent disulfide exchange reactions. Molecular weights were determined by comparison to BENCHMARK™ protein ladder (Invitrogen, Carlsbad, Calif.). The gel was visualized with Coomassie blue stain.

Results

To verify that the introduced cysteines formed disulfide bonds and to show that the disulfide bonds were intramolecular, SDS-PAGE was run on redox-sensitive GFP #2 (rosGFP2), harboring the mutations C48S/S65T/S147C/Q204C, and on a control GFP (C48S/S65T) under reducing and non-reducing conditions. If an intramolecular disulfide bond forms, the resulting polypeptide would be expected to migrate further based on its slightly more compact structure in the denatured form. However, if an intermolecular disulfide bridge forms, then a large molecular weight band (~60 kDa) corresponding to a disulfide-linked dimer, would be expected.

Figure 4:
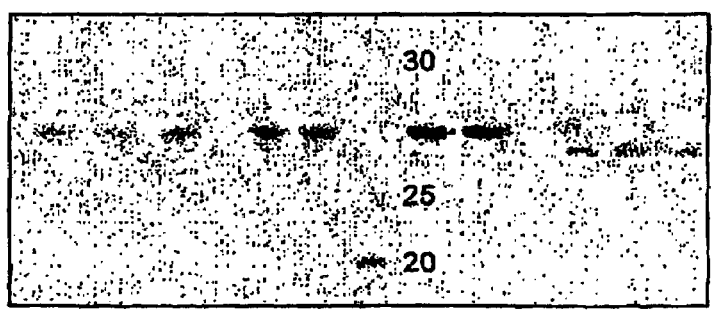
FIG. 4 shows an SDS-PAGE analysis that reveals the intracellular disulfide linkage in rosGFP2. Lanes 1–6, control (C48S/S65T) and lanes 8–13 rosGFP2 were incubated with 1 $\mu$M CuCl2 (with or without 2 mM N-ethylmaleimide; lanes 2, 3, 11, 12) or with 1 mM DTT (with or without 2 mM N-ethylmaleimide; lanes 5, 6, 8, 9). Lane 7 shows approximate molecular weights in kDa. Lanes 4 and 10 were empty.

The results (FIG. 4) indicate that the introduced cysteines form intramolecular disulfide cross-links, but are unable to produce disulfide-linked dimers. This can be seen by comparing lanes 11 and 12 with lanes 14–16 or lanes 21 and 22 with lanes 17–19 (FIG. 4).

Example 4

Determination of Redox Potentials

Apparent redox potential values for the rosGFPs were found by exploiting the fact that the fluorescence of the rosGFP chromophores is strongly dependent upon the redox state of the introduced cysteines. Therefore the redox equilibrium of the rosGFPs with dithiothreitol ($DTT_{red}$) and oxidized dithiothreitol ($DTT_{ox}$) was analyzed. The equilibrium for the oxidation of reduced rosGFP by $DTT_{red}$ and its equilibrium constant ($K_{eq}$) are given by equations 1 and 2.

$$rosGFP_{red} + DTT_{ox} \rightleftharpoons rosGFP_{ox} + DTT_{red} \quad (1)$$

$$K_{eq} = [rosGFP_{ox}][DTT_{red}]/[rosGFP_{red}][DTT_{ox}] \quad (2)$$

Figure 20:
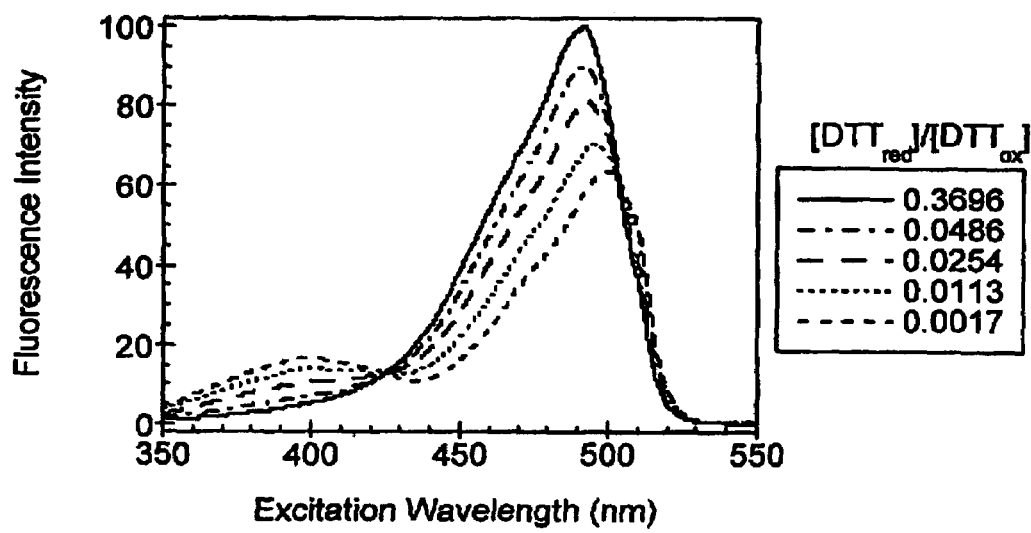
FIG. 20. Fluorescence excitation spectra of rosGFP2 at varying concentrations of $DTT_{red}$ and $DTT_{ox}$. Fluorescence emission intensity was monitored at 510 nm and normalized to the maximum intensity of the fully reduced spectrum (solid line).

When rosGFPs were incubated in the presence of varying concentrations of $DTT_{red}$ and $DTT_{ox}$ (total $DTT_{red}$+$DT$-$T_{ox}$=1 mM), the fractional amount of reduced rosGFP at equilibrium (R) could be measured over the whole range from the oxidized to the reduced protein using the chromophore fluorescence (FIG. 20). Based on the SDS-PAGE result hat indicated rosGFPs only form intramolecular disulfide bonds, R can be related to $K_{eq}$ by equation 3 (Hawkins et al., Biochem J 1991 275(2):341–348).

$$R = ([DTT_{red}]/[DTT_{ox}])/(K_{eq} + [DTT_{red}]/[DTT_{ox}]) \quad (3)$$

For experimental determination of the equilibrium constants of the GFP:dithiothreitol system, the equilibrium concentrations of $DTT_{red}$ and $DTT_{ox}$ were calculated according to equations 4–6, where $[DTT_{red\,o}]$ and $[DTT_{ox\,o}]$ are the initial concentrations of $DTT_{red}$ and $DTT_{ox}$, respectively, R is the fractional amount of reduced rosGFP at equilibrium, [rosGFP$_o$] is the initial concentration of oxidized rosGFP, F is a fluorescence intensity ratio of band B excitation (490 nm) versus the isosbestic point (425 nm), and $F_{ox}$ and $F_{red}$ are the 490:425 nm ratios of the completely oxidized and reduced protein, respectively. By plotting R against the $$[DTT_{red}] = [DTT_{red\,o}] - R[rosGFP_o] \quad (4)$$

$$[DTT_{ox}] = [DTT_{ox\,o}] + R[rosGFP_o] \quad (5)$$

$$R = (F - F_{ox})/(F_{red} - F_{ox}) \quad (6)$$

Figure 21:
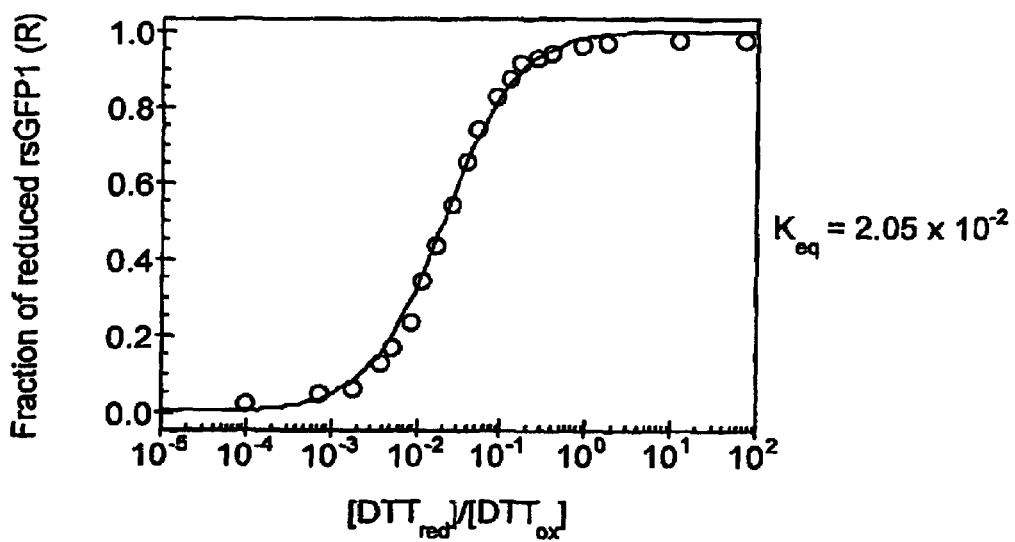
FIG. 21. Redox equilibrium titration of rosGFP2 with dithiothreitol. The relative amount of reduced rosGFP2 at equilibrium (R) was measured using a ratio of the rosGFP2 fluorescence at 510 nm (excitation 490:425 nm). Oxidized rosGFP2 (1 μM) was incubated for four hours in 75 mM HEPES (pH 7.0), 140 mM NaCl, and 1 mM EDTA, containing varying ratios of $DTT_{red}$ to $DTT_{ox}$ (1 mM total). The equilibrium constant was determined by fitting the data according to equation 3. After nonlinear regression, a $K_{eq}$ of $2.05 \times 10^{-2}$ was obtained (correlation coefficient: 0.998).

$[DTT_{red}]/[DTT_{ox}]$ ratio and fitting the data to a titration curve according to equation 3 (FIG. 21), the $K_{eq}$ for the rosGFP1:dithiothreitol system was found to be $2.05 \times 10^{-2}$. The redox potential of rosGFP2 at pH 7 and 30° C. ($E_{o\,rosGFP2}'$) was then calculated from the Nernst equation (7), where $E_o'$ is the biochemist's standard potential of the DTT/DTT$_{ox}$ couple ($E_{oDTT} = -0.323$ V, at pH 7 and 30° C.; Szajewski and Whitesides 1980), R is the gas constant (8.315 J K$^{-1}$ mol$^{-1}$), T is the absolute temperature (303.15 K), n is the number of transferred electrons (2), and F is the Faraday constant ($9.649 \times 10^4$ C mol$^{-1}$) and found to be −0.272 V.

$$E_{o\,rosGFP2}' = E_{oDTT}' - (RT/nF) \times \ln K_{eq} \quad (7)$$

Redox potentials involving the liberation of H$^+$ ions are intrinsically based on pH. The pH-dependence on the redox potential is more apparent when examining the two half-reactions involving rosGFP and DTT (equation 8 and 9).

$$rosGFP_{ox} + 2H^+ + 2e^- \rightleftharpoons rosGFP_{red} \quad (8)$$

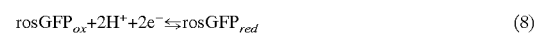

$$DTT_{red} \rightleftharpoons DTT_{ox} + 2H + 2e^- \quad (9)$$

At equilibrium the concentrations of rosGFP$_{ox}$ and rosGFP$_{red}$ are equal and thus the $K_{eq}$ is equal to the $[H+]^2$. The standard redox potential of rosGFP2 ($E_{o\,rosGFP2}$) at pH 0 could then be determined from equation 10.

$$E_{o\,rosGFP2} = E_{o\,rosGFP2}' - (RT/nF) \times \ln K_{eq} \quad (10)$$

$E_{o\,rosGFP2}$ was calculated to be 0.149 V. Equation 11 simplifies the expression for the pH-dependence of redox potentials involving two protons.

$$E_o^{pH} = E_o' - 60.2\,mV \times (pH-7) \quad (11)$$

The pH-dependence on the redox potential therefore changes 60.2 mV with each pH unit. Experimentally $E_o$ rosGFP2 varied 65.5 mV per pH unit from pH 6 to 8 (correlation coefficient: 0.9999). Therefore, although a linear correlation between pH and $E_{o\,rosGF2}$ is observed, the pH-dependence of the rosGFP2 standard potential does not directly correspond to this model. The deviation from this model for the pH-dependence of $E_o$ may be due in part to the contributions of charged residues near the introduced disulfide of rosGFP2 as well as potentially different $pK_a$ values for the cysteine residues (Wunderlich and Glockshuber, *Protein Sci* 2(5):717–726, 1993; Wunderlich and Glockshuber, *J Biol Chem* 268(33):24547–24550, 1993)

Example 5

Spectral Analysis of rosGFPs

Spectroscopy and pH Titrations

Absorbance measurements were performed on a Shimadzu 2101 spectrophotometer. The molar extinction coefficient of GFP S65T ($\lambda_{280\ nm}$=19,890 $M^{-1}$ $cm^{-1}$) was calculated from its amino acid sequence as previously described (Gill and von Hippel, *Anal. Biochem.* 182:319–326, 1989), and used to determine protein concentrations of the rosGFPs. pH titrations were performed using approximately 200 μg $mL^{-1}$ mutant GFP in 75 mM buffer, 140 mM NaCl and either 1 μM $CuCl_2$ or 5 mM DTT. According to the desired pH, an appropriate buffer was chosen from MES, HEPES, or CHES and the final pH was adjusted by addition of HCl or NaOH. The absorbance was then scanned between 250 and 550 nm and the optical density of the long-wave band B was plotted as a function of pH and fitted to a titration curve to obtain $pK_a$ values.

Fluorescence excitation spectra at various pHs were attained on a Hitachi F4500 fluorescence spectrophotometer or a Perkin Elmer LS 55 luminescence spectrometer at protein concentrations of approximately 100 μg $mL^{-1}$ in the same buffers used for absorbance measurements. Apparent chromophore $pK_a$ values were determined by plotting the emission intensity when excited at band B as a function of pH and fitting the data to a titration curve (KALEIDA-GRAPH™ scientific graphing software). In all cases, the $pK_a$ values determined by absorbance and fluorescence differed by no more than +/−0.05 of a pH unit. All plots and curve fits were made with KALEIDAGRAPH™ scientific graphing software (Abelbeck Software).

Redox Titrations

Fluorescence measurements were performed at 30° C. using a thermostated cuvette holder. Samples consisted of 1 μM GFP in 75 mM HEPES (pH 7.0), 140 mM NaCl, 1 mM EDTA, and 1 mM total DTT (mixture of oxidized and reduced forms). To exclude air oxidation, the solutions were degassed and subsequently flushed with nitrogen. In general equilibration was reached within one hour at pH 7.0. Equilibration of rosGFPs was ensured by incubating the samples at 30° C. for four hours. The reaction appeared to be at equilibrium, since the ratio of oxidized and reduced protein, as determined by fluorescence, did not change between 4 and 16 hour incubation times.

Spectral Characteristics

Figure 5A:
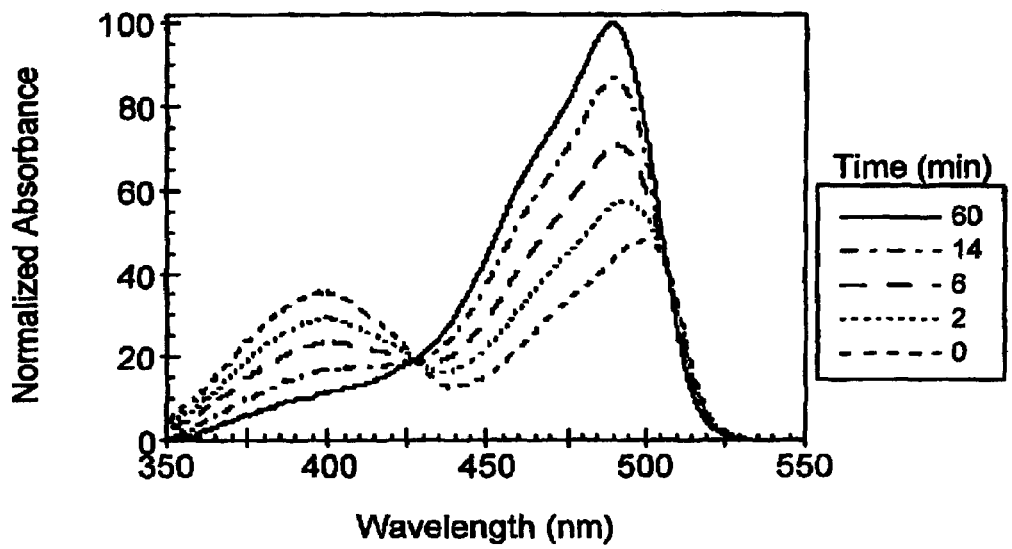
FIG. 5. Absorbance and fluorescence excitation spectra of rosGFP2 at various redox states. The absorbance spectra (A) show the conversion of the neutral (band A; 400 mn) to the anionic (band B; 490 nm) chromophore species over time in the presence of 1 mM DTT. Band A is maximized under oxidizing conditions, whereas band B is favored under reducing conditions. Fluorescence spectra (B) were collected at various redox potentials and also show the interconversion of chromophore charge states. Absorbance and fluorescence spectra were both normalized to the intensity of the fully reduced protein.
Figure 5B:
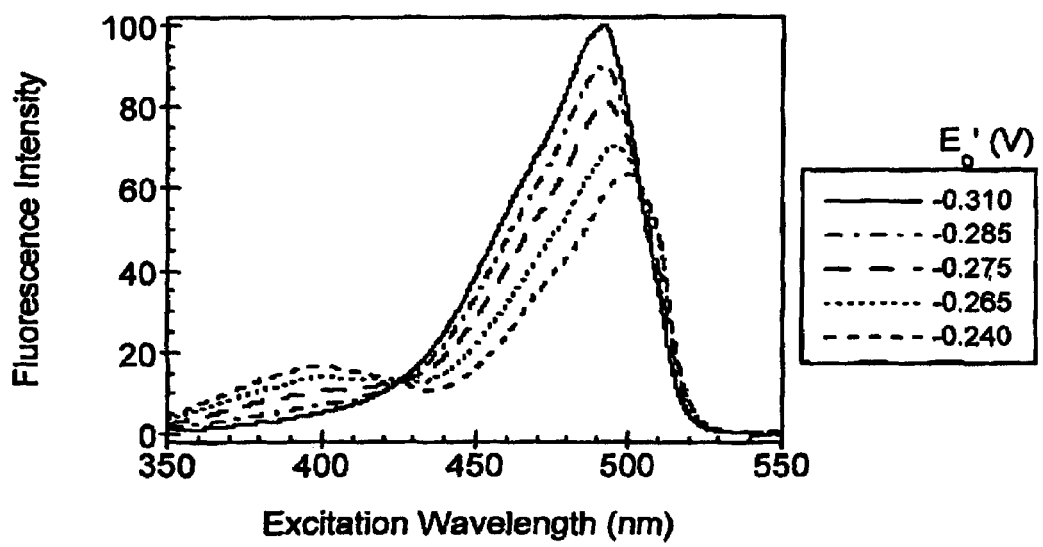

To test whether the introduced cysteines affect the spectral properties of GFP, absorbance and fluorescence scans were collected at varying redox potentials. To establish various redox potentials, GFP was equilibrated with varying concentrations of dithiothreitol (DTT) and oxidized DTT (DT-$T_{ox}$) FIG. 5 shows the absorbance and fluorescence excitation spectra of rosGFP2 as a function of redox potential. With a disulfide bond formed under oxidizing conditions, the 400 nm peak (band A) was maximized whereas the 490 nm peak (band B) was minimized. Conversely, in the absence of a disulfide cross-link achieved with reducing conditions, band B was at a maximum, while band A was at a minimum. The two peaks were separated by a clean isosbestic point at 425 nm, indicative of two species interconverting. The redox potential of rosGFP2 was then determined from the equilibrium constant obtained by plotting the fraction of reduced protein versus the ratio of $DTT_{red}$ to $DTT_{ox}$ (see Example 4) and discovered to be −0.272 V.

Figure 6A:
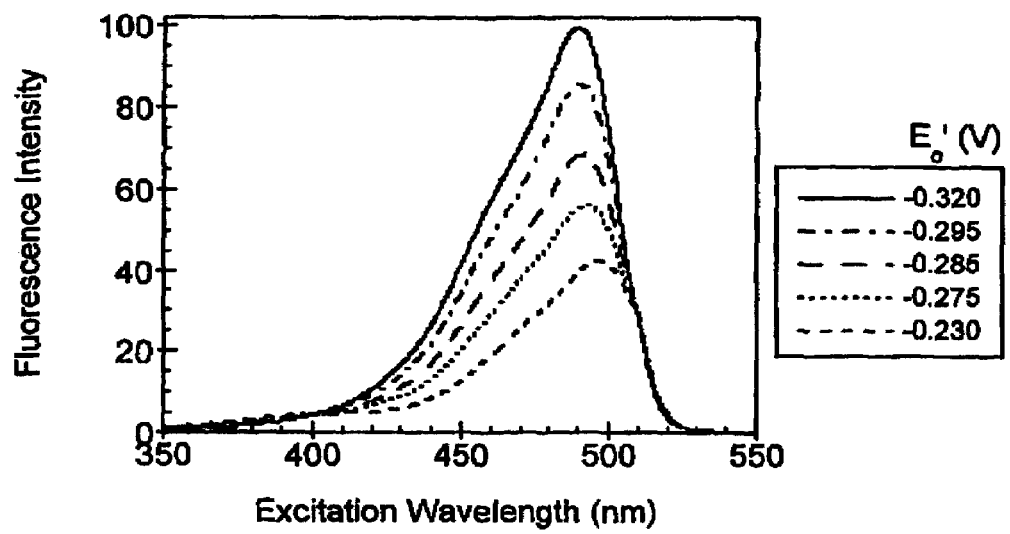
FIG. 6. Fluorescence excitation spectra of rosGFP4 as a function of redox potential. The entire spectrum (A) shows the redox potential dependence on the excitation spectra of rosGFP4. Expanded the region around 400 nm (B), reveals a well resolved isosbestic point. Fluorescence intensity values were normalized to the maximum intensity at $E_o'$−0.320 V and emission was monitored at 510 nm.
Figure 6B:
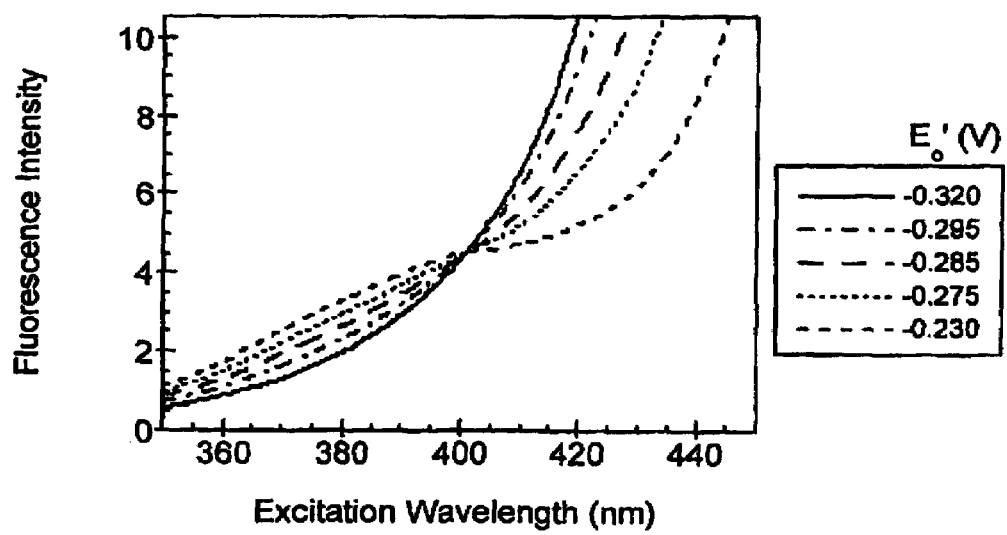

Introducing a pair of cysteines at the alternative site also yielded a mutant protein whose fluorescent properties varied in response to redox potential (FIG. 6A). The rosGFP4 variant, having the mutations C48S/S65T/N149C/S202C, displayed increased band B fluorescence over rosGFP2, however band A fluorescence intensity was almost non-existent The fluorescence isosbestic point of rosGFP4 was shifted to approximately 400 nm (FIG. 6B).

Figure 7:
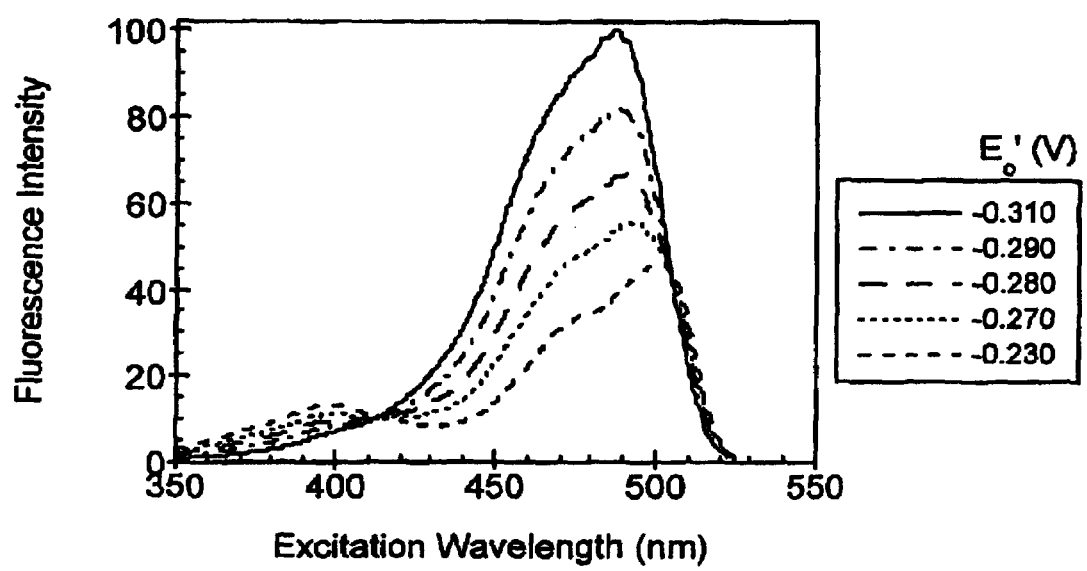
FIG. 7. Fluorescence excitation spectra of rosGFP6 as a function of redox potential. Fluorescence intensity values were normalized to the maximum intensity at $E_o'$−0.310 V and emission was monitored away from the peak at 535 nm.

Combining the two pairs of cysteine substitutions resulted in a variant (C48S/S65T/S147C/N149C/S202C/Q204C, rosGFP6), whose properties appeared to be an average of both rosGFP2 and rosGFP4. FIG. 7 shows the fluorescence excitation spectra of rosGFP6. In this variant the dynamic range of the two excitation peaks as well as the isosbestic point lie in the middle of the values observed for either rosGFP2 or rosGFP4.

The overall dynamic range of the excitation ratio (δ), determined by dividing the maximum and minimum possible excitation peak ratios, was found to be 5.4 for rosGFP6. Table 5 summarizes the spectroscopic and biochemical parameters of the rosGFP variants.

TABLE 5

Spetroscopic and Biochemical Properties of rosGFPs.

| Name | Mutations[1] | $K_{eq}^2$ | $E_o^1(V)^3$ | $\delta^4$ |
|---|---|---|---|---|
| rosGFP2 | S65T/S147C/Q204C | 0.0205 | −0.272 | 5.8 |
| rosGFP1 | S147C/Q204C | 0.0702 | −0.288 | 6.1 |
| rosGFP4 | S65T/N149C/S202C | 0.0561 | −0.286 | 2.6 |
| rosGFP3 | N149C/S202C | 0.1505 | −0.299 | 4.3 |
| rosGFP6 | S65T/S147C/N149C/S202C/Q204C | 0.0385 | −0.280 | 5.4 |
| rosGFP5 | S147C/N149C/S202C/Q204C | 0.1341 | −0.296 | 7.8 |

[1]All variants contain the phenotypically neutral C48S and Q80R substitutions
[3]Equilibrium constant ($K_{eq}$) values refer to equilibration of rosGFPs with the $DTT_{red}/DTT_{ox}$ couple.
[3]Redox potentials ($E_o^1$) were calculated at pH 7 and 30° C. using the $K_{eq}$ for the GFP-dithiothreitol system (see Appendix).
[4]δ is the maximum excitation peak ratio change in number of fold.

pH-Sensitivity of rosGFPs

Figure 8A:
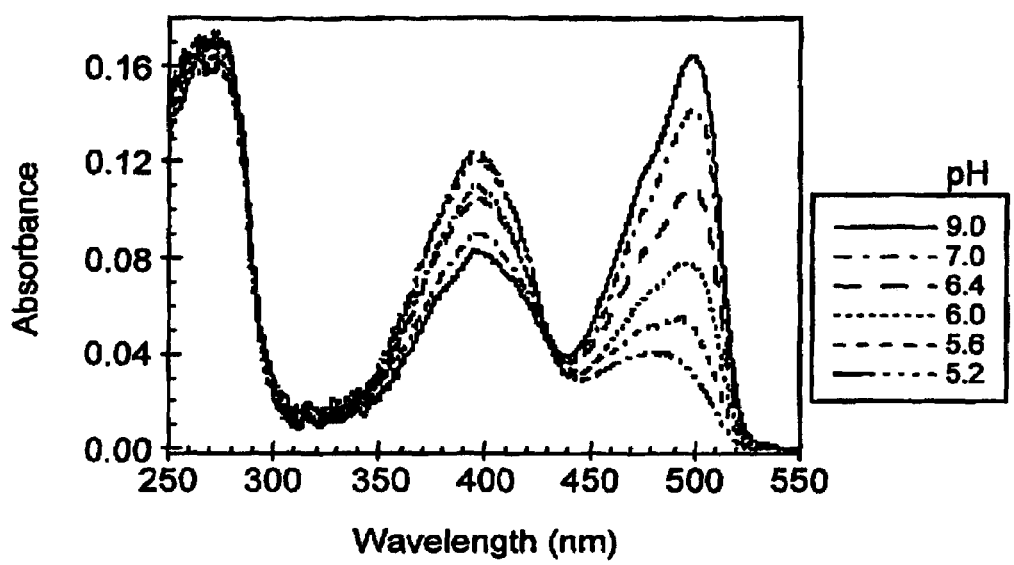
FIG. 8. Absorbance and fluorescence excitation spectra of oxidized rosGFP2 as a function of pH. Absorbance scans (A) were taken on samples of rosGFP2 containing 0.5 $\mu$M $CuCl_2$ at the indicated pHs. These samples were then diluted in the same buffer and their fluorescence excitation spectra (B) were collected. Fluorescence intensity values were normalized to the maximum intensity at pH 9.0 and emission was monitored at 510 nm.
Figure 8B:
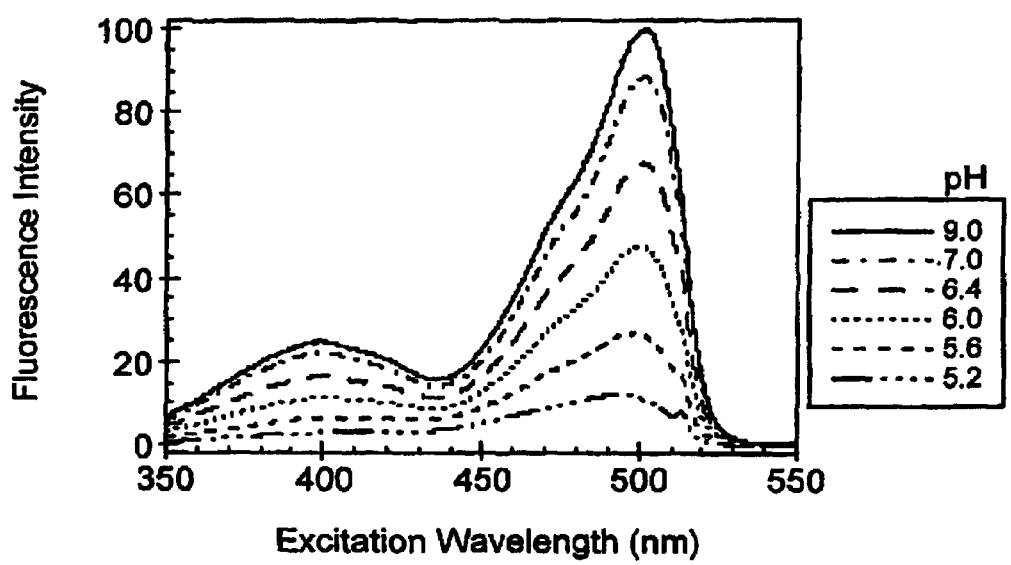
Figure 9A:
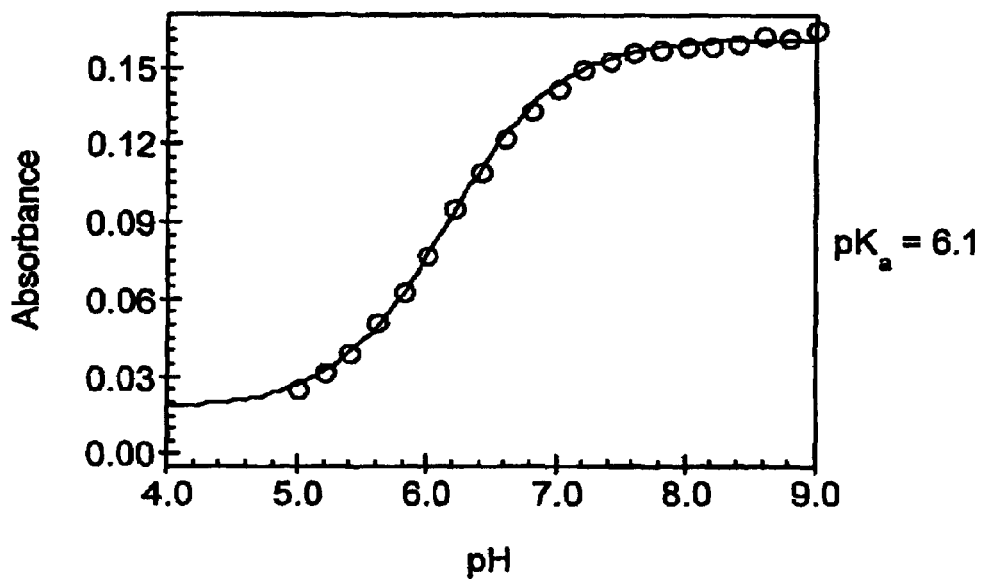
FIG. 9. pH titration of oxidized and reduced rosGFP2. Absorbance values at 490 nm (band B) were plotted versus pH for oxidized (A) and reduced (B) rosGFP2. The data were then fitted to a titration curve with a single $pK_a$ value.
Figure 9B:
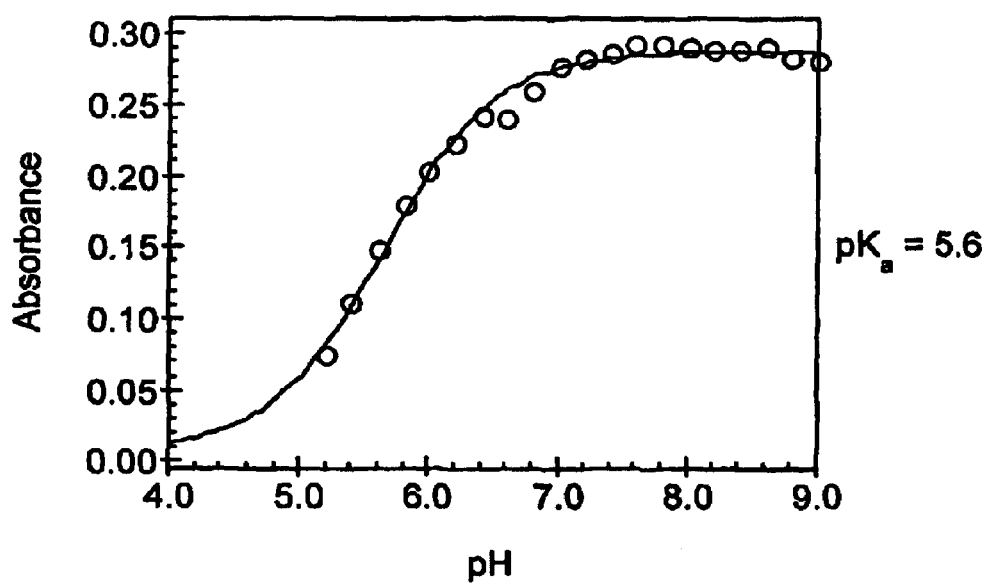
Figure 10A:
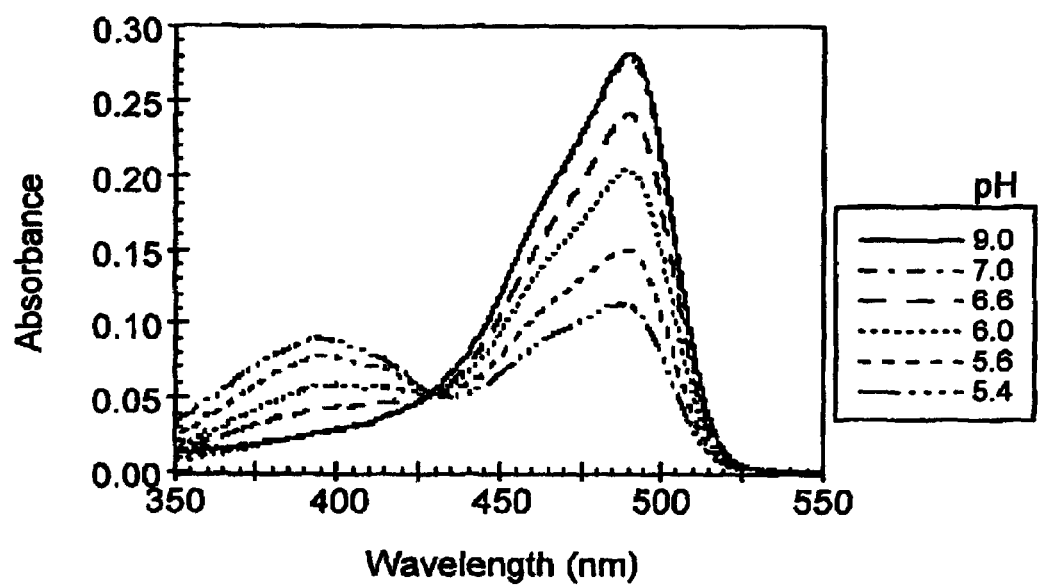
FIG. 10. Absorbance and fluorescence excitation spectra of reduced rosGFP2 as a function of pH. Absorbance scans (A) were taken on samples of rosGFP2 containing 1 mM DTT at the indicated pHs. These samples were then diluted in the same buffer and their fluorescence excitation spectra (B) were collected. Fluorescence intensity values were normalized to the maximum intensity at pH 9.0 and emission was monitored at 510 nm. Absorbance readings around 280 nm are greatly altered due to the presence of DTT and thus are not shown.
Figure 10B:
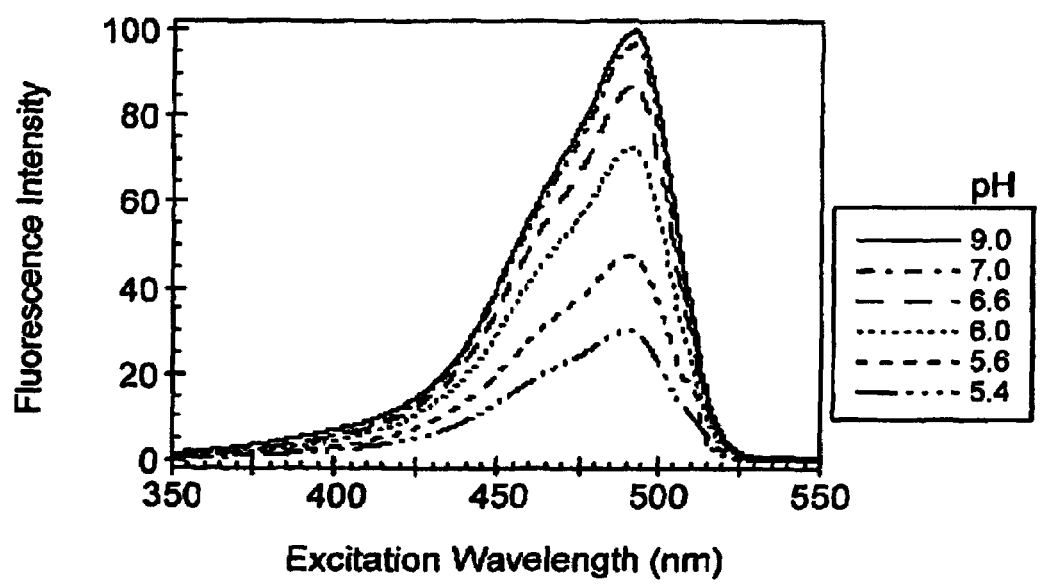

Previous work has shown that, while the fluorescence of wild-type GFP is unaffected throughout the biologically relevant pH range from 6 to 8 (Ward and Bokman, *Photochem. Photobiol.* 35:803–808, 1982), GFP variants harboring the S65T mutation often exhibit dramatic fluorescence changes over this pH range (Kneen et al., *Biophys. J.* 74:1591–1599, 1998; Wachter et al., *Structure* 6:1267–1277, 1998; Elsliger et al., *Biochemistry* 38:5296–5301, 1999). To determine if the rosGFPs were also pH-sensitive, their absorbance and fluorescence were scanned over a wide range of pHs. FIG. 8 shows both absorbance and fluorescence excitation spectra of oxidized rosGFP2 versus pH. The spectra show that, as the pH is increased from 5.2 up to 9.0, the fluorescence intensity of both excitation peaks increases. Plotting the intensity at 490 nm as a function of pH and fitting this to a titration curve with a single ionization constant gave a $pK_a$ value of 6.0 (FIG. 9). Titration of rosGFP2 in the reduced state shifted the $pK_a$ to 5.6 (FIG. 10).

Initially it appeared that the pH-sensitivity of the rosGFPs might pose a problem for using them as tools to determine in vivo redox potentials by introducing pH artifacts. Therefore, to produce a pH-insensitive rosGFP, threonine 65 was reverted back to serine, which is the amino acid found at this position in wild-type GFP.

Figure 11:
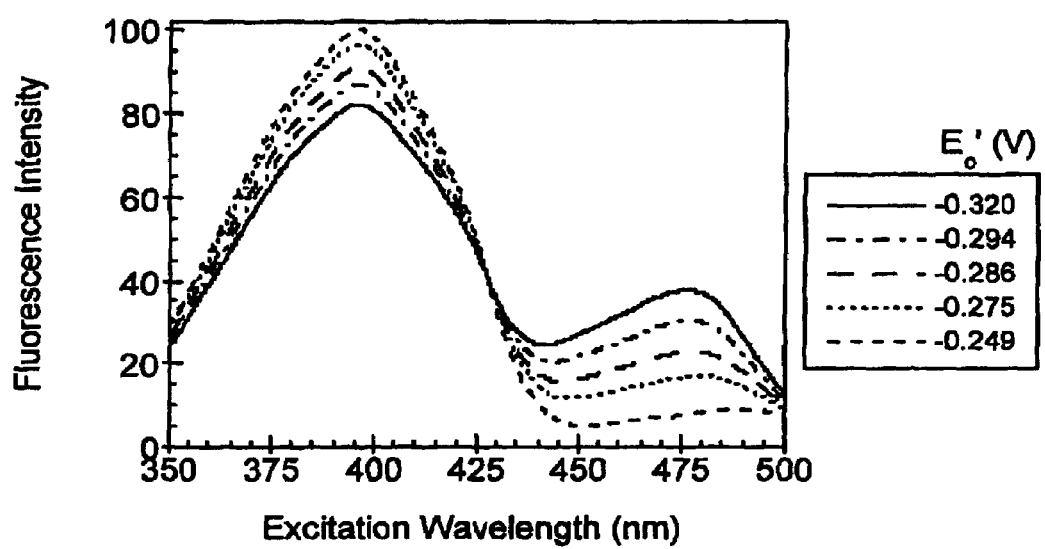
FIG. 11. Fluorescence excitation spectra of rosGFP1 at various redox potentials. Fluorescence intensity values were normalized to the maximum intensity at $E_o'$−0.320 V and emission was monitored at 510 nm.
Figure 12A:
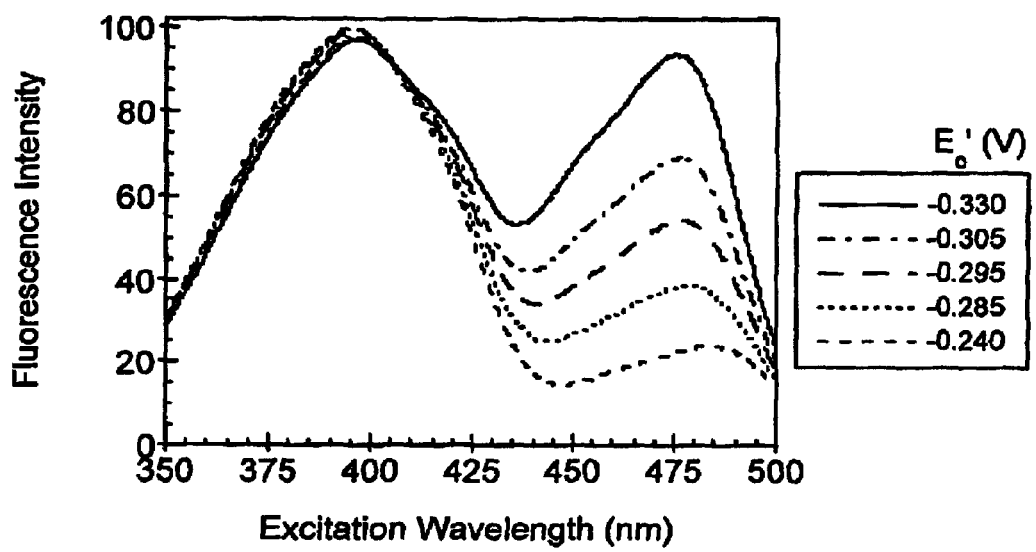
FIG. 12. Fluorescence excitation spectra of rosGFP3 at various redox potentials. The entire spectrum (A) shows the redox potential dependence on the excitation spectra of rosGFP3. Expanded the region around 405 nm (B), reveals the existence of an isosbestic point. Fluorescence intensity values were normalized to the maximum intensity at $E_o'$-0.330 V and emission was monitored at 510 nm.
Figure 12B:
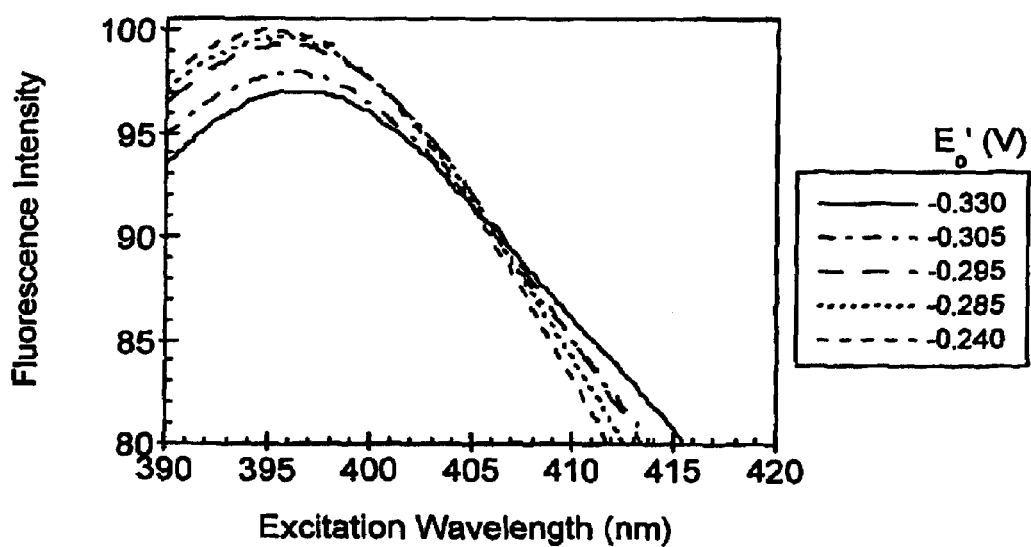
Figure 13:
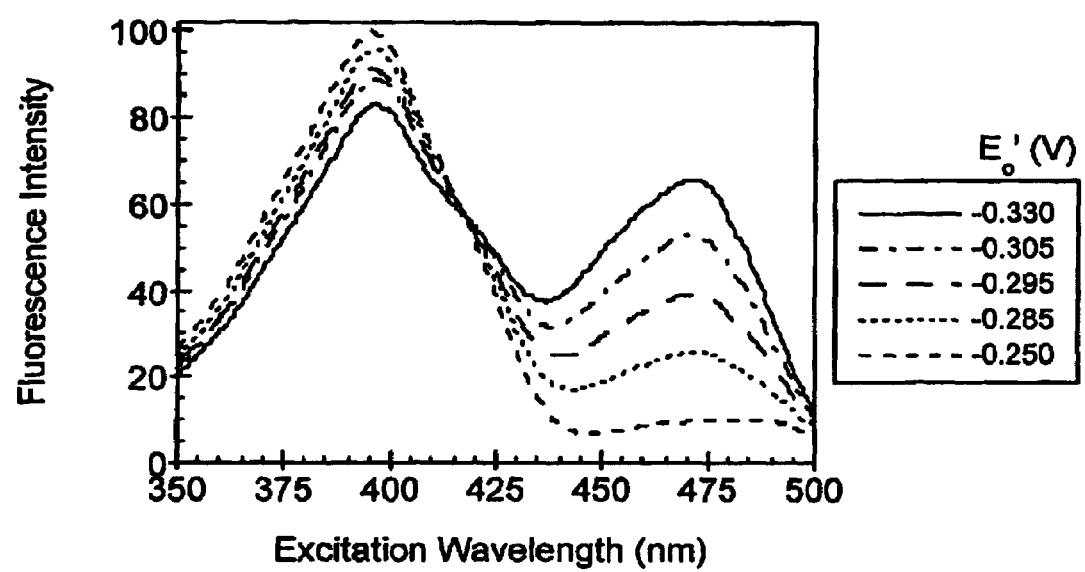
FIG. 13. Fluorescence excitation spectra of rosGFP5 at various redox potentials. Fluorescence intensity values were normalized to the maximum intensity at $E_o'$-0.330 V and emission was monitored off the peak at 535 nm.

Not only did the T65S reversion completely eliminate pH-sensitivity over the range of 6 to 8, but it greatly altered the spectral properties of the rosGFPs. FIGS. 11, 12, and 13 show the fluorescence excitation spectra of rosGFP1 (C48S/S147C/Q204C), rosGFP3 (C48S/N149C/S202C), and rosGFP5 (C48S/S147C/N149C/S202C/Q204C) at varying redox potentials. The most striking difference between these rosGFPs and threonine 65 containing rosGFPs is the favoring of band A over band B fluorescence. There is also a tendency toward more even excitation of both bands, which is especially evident in the rosGFP3 and rosGFP5 variants. Unexpectedly, the T65S reversion led to a 13–16 mV more reducing redox potential (see Table 5).

Figure 14A:
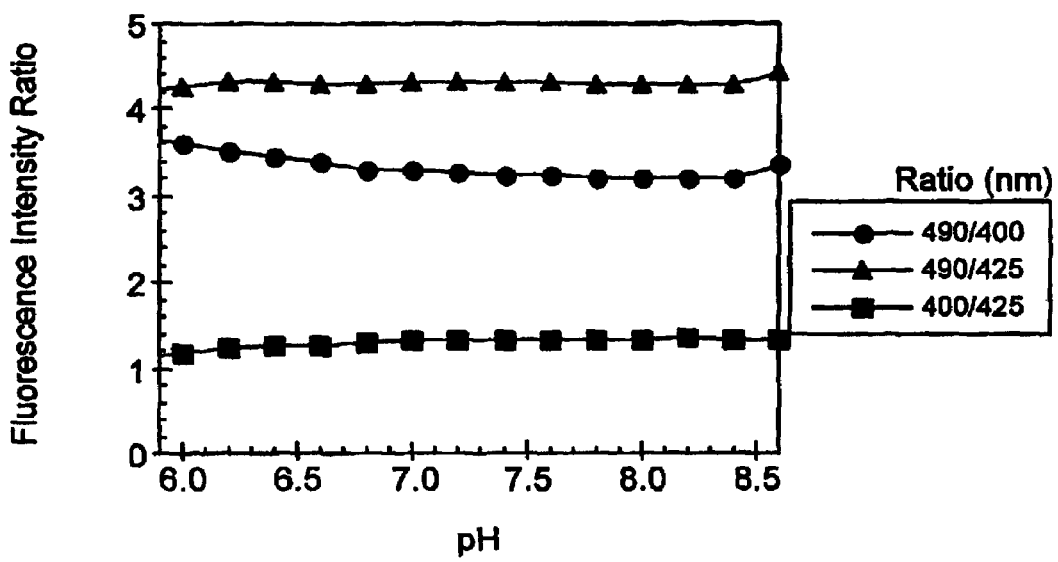
FIG. 14. A fluorescence excitation ratio results in the cancellation of pH artifacts. In the oxidized (A) or reduced (B) state, a ratio of fluorescence intensities at various excitation wavelengths of rosGFP2 is independent of pH.
Figure 14B:
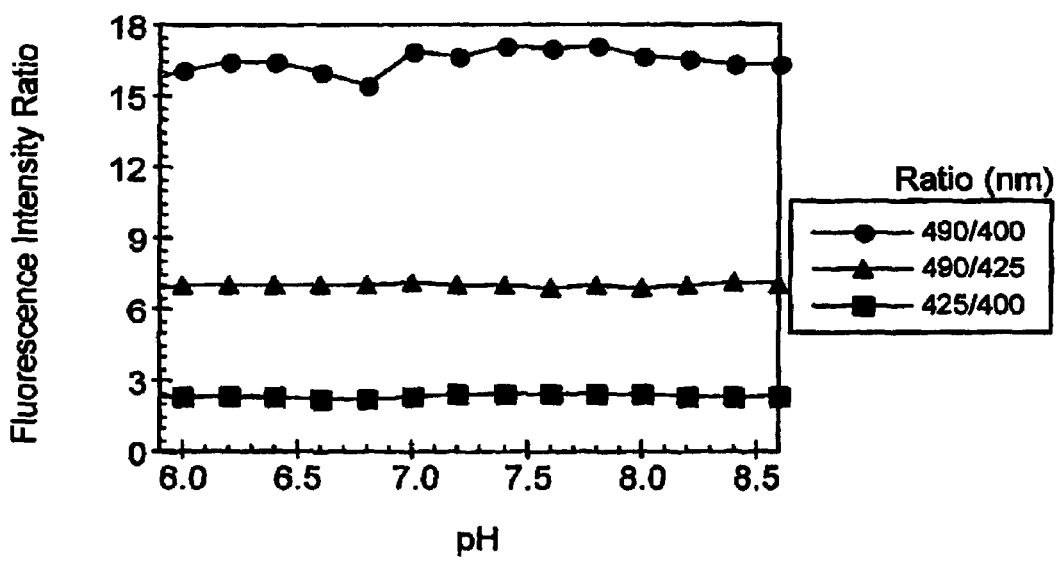

Subsequent to construction of the variants containing the T65S reversion, it was determined that, by using a fluorescence excitation ratio, any effects induced by pH changes were virtually eliminated. FIG. 14 illustrates how the ratio of excitation wavelengths remains a constant over a large pH range in both the fully reduced or fully oxidized protein. In other words, the fluorescence increase due to alkalization or fluorescence decrease upon acidification seen in the excitation spectra of rosGFP2 affects the entire spectrum in the same manner, and hence the ratio of intensities is unaffected by pH changes in the range of at least pH 6 to 8.5. Therefore, a ratio of the excitation wavelengths cancels out variations due to pH fluctuations and allows for redox status determination in the absence of pH artifacts.

Figure 15:
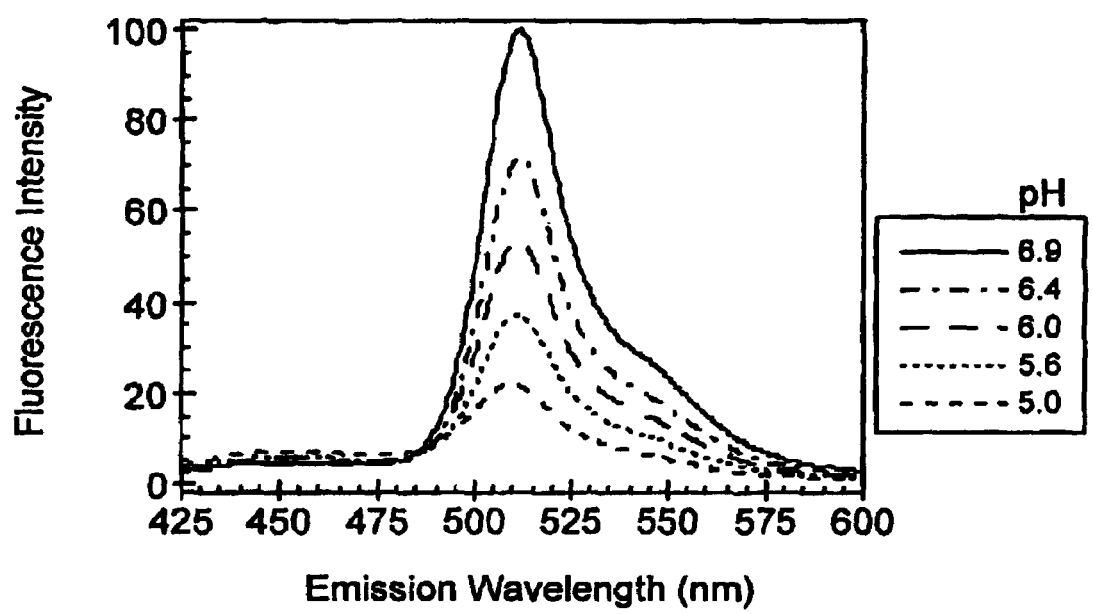
FIG. 15. Dual-emission characteristics of rosGFP2. Excitation at 400 nm results in emission peaks centered near 450 and 510 nm, which have an opposite response to pH changes.
Figure 16A:
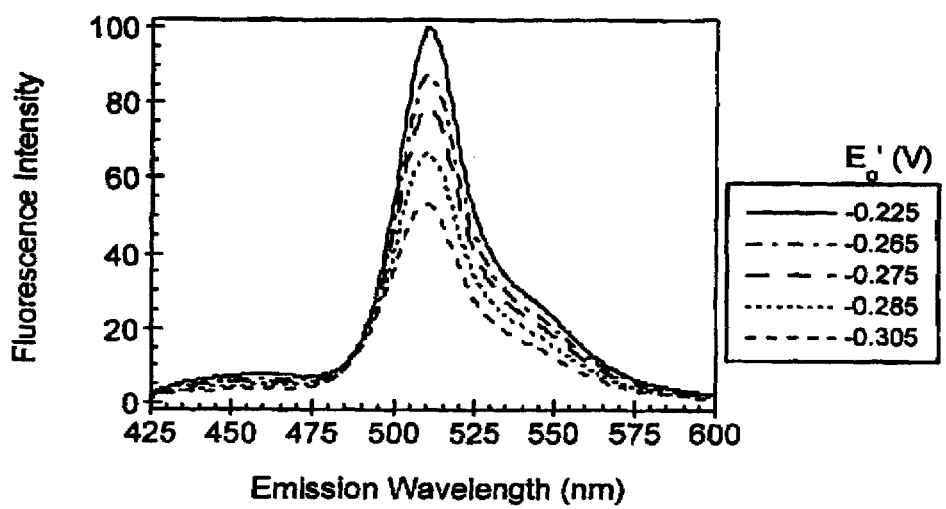
FIG. 16. A fluorescence emission ratio results in the cancellation of redox potential changes on pH determination. The fluorescence emission spectra (A) of rosGFP2 were collected at various redox potentials (ratios of DTT and $DTT_{ox}$) and at a constant pH of 6.0. Plotting the ratio of the two emission peaks results in a constant ratio over a large range of redox states (B). The dashed lines in B represent the maximum and minimum ratios to illustrate the possible dynamic range of rosGFP2 as a function of pH.
Figure 16B:
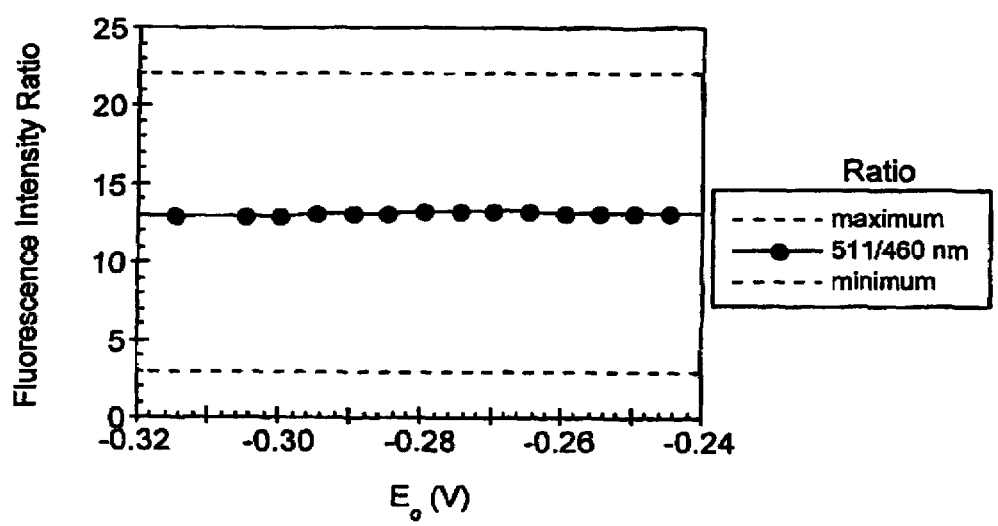

Since redox reactions involving the liberation of $H^+$ ions are intrinsically based on pH (see Example 4), and consequently the pH of the cellular compartment of study must be determined, the ability to separate out the pH and redox sensing capabilities of rosGFP2 was investigated. Excitation of band A was found to result in pH-dependant dual-emission (FIG. 15). In other words, at low pH, blue emission prevails and at high pH, green emission dominates, with $pK_a$s of 5.6 (reduced) to 6.0 (oxidized) dependant upon the redox state of rosGFP2. This phenomenon is a useful means of monitoring pH changes in vivo. By utilizing a ratio of emission wavelengths, pH variations due to the redox state of the probe are minimized (FIG. 16). Therefore, it is possible to experimentally separate out the pH and redox contributions to the fluorescent signal, and thus simultaneous monitoring of redox and pH is possible with the same probe.

Example 6

Structural Basis for Dual-Excitation

The crystal structure of rosGFP2 was solved in order to better understand how disulfide bond formation leads to dual excitation. Crystals belonging to the space group $P2_12_12$ were grown of both the oxidized and reduced forms of rosGFP2 and the crystal structures were solved by molecular replacement to 1.9 Å and 2.0 Å, respectively. The protein crystallized as a dimer, with three molecules in the asymmetric unit. One molecule is related to its dimer mate by a crystallographic two-fold axis of symmetry, and the other dimer is related to itself by a non-crystallographic two-fold axis of symmetry.

Since the resolution limit of the data collected was fairly high, refinement was performed without imposing any non-crystallographic symmetry constraints, and thus each of the three molecules in the asymmetric unit were independently refined. Analysis of the different molecules in the asymmetric unit after refinement revealed only very subtle differences, all of which were within experimental error (approximately 0.2 Å) for the atomic positions at his resolution. Interestingly, the surface facing a solvent channel of one of the molecules comprising the non-crystallographic symmetry dimer is very poorly ordered This disorder is most certainly reflected in many of the refinement statistics presented in Table 6.

TABLE 6

Data Collection and Refinement Statistics for Oxidized and Reduced rosGFP2.

Data Collection

| Crystal | Oxidized | Reduced |
|---|---|---|
| Total observations | 203,865 | 194,884 |
| Unique reflections | 56,854 | 38,346 |
| Cell dimensions (a, b, c; Å) | 186.84, 67.61, 56.08 | 185.63, 67.86, 56.38 |
| Resolution (Å) | 29.7–1.90 | 28.7–2.00 |
| Highest resolution shell (Å) | 1.95–1.90 | 2.10–2.00 |
| Completeness[1] (%) | 99.8 (100) | 78.2 (74.3) |
| Multiplicity[1] | 3.6 (3.6) | 5.1 (5.5) |
| Average I/σ[1] | 7.2 (2.3) | 8.7 (2.2) |
| $R_{merge}$[1,2] | 0.058 (0.247) | 0.053 (0.304) |

Refinement

| Spacegroup | $P2_12_12$ | $P2_12_12$ |
|---|---|---|
| Number of molecules[3] | 3 | 3 |
| Number of protein atoms[3] | 5,220 | 5,216 |
| Number of solvent atoms[3] | 174 | 132 |
| $R_{factor}$[4] | 0.229 | 0.223 |
| Average B-factors (Å$^2$) | 46.6 | 49.7 |
| Protein atoms | 46.7 | 49.7 |
| Solvent | 44.2 | 47.4 |
| rms deviations | | |
| Bond lengths (Å) | 0.020 | 0.014 |
| Bond angles (°) | 3.111 | 2.436 |
| B-factor correlations (Å$^2$) | 7.019 | 5.779 |

[1]Values in parentheses indicate statistics for the highest resolution shell.
[2]$R_{merge} = \Sigma |I-<I>|/\Sigma <I>$, where I is the observed intensity, and <I> is the average of intensity obtained from multiple observations of symmetry related reflections.
[3]Per asymmetric unit.
[4]$R_{factor} = \Sigma ||F_o|-|F_c||/\Sigma |F_o|$, where $F_o$ and $F_c$ are the observed and calculated structure factors, respectively.

The dimer interface is essentially the same as seen for wild-type GFP and the yellow variant of GFP (Yang et al., *Nature Biotech.* 14:1246–1251, 1996; Wachter et al., *Structure* 6:1267–1277, 1998). One molecule of the dimer is tilted approximately 70 degrees with respect to the other molecule based on an imaginary axis drawn from one end of the GFP barrel structure through the center and out the other end. The dimer interface is comprised of a small hydrophobic patch consisting of alanine 206, leucine 221 and phenylalanine 223, a hydrogen bond interaction between tyrosine 39 and aspartame 149, as well as a number of hydrophilic contacts involving several bound water molecules. At present it is not known whether the dimer is solution relevant or simply an artifact created by the crystallization conditions (Palm and Wlodawer, *Nat. Struct. Biol.* 4:361–365, 1997). At any rate, knowledge of the dimer interface residues permits future mutational studies aimed at disrupting dimers without affecting protein stability and folding.

As expected, the introduced cysteines are positioned toward the outside of the protein and are in excellent arrangement to form a disulfide bond under oxidizing conditions. They reside along the edge of the dimer interface and adjacent to bulk solvent. The individual disulfides are separated by 14 Å from the opposing dimer pair of cysteines and therefore, as shown by gel electrophoresis, are unable to form intermolecular disulfide bonds and are unlikely to aid in dimer formation. The disulfide bond present in the oxidized structure does not have ideal geometry, with an average $C_\alpha$—$C_\alpha$ distance of 4.0 Å, $C_\beta$—$C_\beta$ distance of 4.2 Å, S—S distance of 2.0 Å, $C_\alpha$—$C_\beta$—S angle of 112°, and $C_\beta$—S—S angle of 106°. These parameters diverge from those values seen in other structures of disulfide bond-containing proteins (Sowdhamini et al. 1989; Matsumura et al. 1989), and may also account for or contribute to the observed spectral perturbations.

Example 7

Mammalian Cell Expression and Fluorescence Microscopy

The mutations C48S/T65S/S147C/Q204C were introduced into the mammalian expression plasmid pEGFP-N1 (CLONTECH, Palo Alto, Calif.). This plasmid has the "folding mutation" F64L, which was found not to alter the spectral or redox properties of the rosGFPs. HeLa cells transiently transfected with this plasmid using Fugene (Boehringer-Mannheim, Germany) were imaged one day post-transfection on a motorized Zeiss Axioscope 2 microscope. The temperature of the cells was maintained at 37° C. using an open perfusion micro-incubator (Harvard Apparatus Inc., Holliston, Mass.). Dual-excitation ratio imaging required 400(10) and D480/30× excitation filters, a 505DCXR dichroic mirror, and a D535/40m emission filter (Edmund Scientific Company, Omega Optical and Chroma Technologies, Battleboro, Vt.) alternated by a fast filter changer. Images were collected with a PentaMax cooled CCD camera (Princeton Instruments). Data was collected and processed using the program Openlab (Improvision, Lexington, Mass.).

In vivo Redox Status

Figure 17:
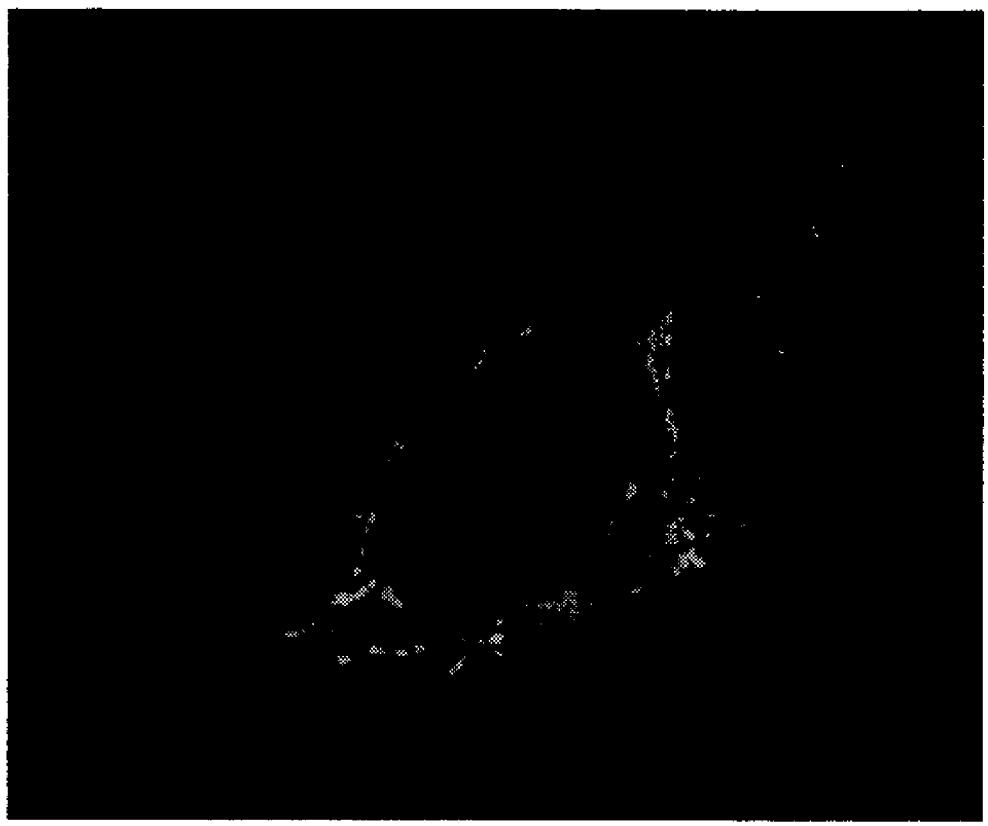
FIG. 17. A fluorescent micrograph showing the reticular localization pattern of rosGFP1 expressed in the mitochondrial matrix of an in vitro cultured HeLa cell, via fusion at the DNA level to the mitochondrial targeting sequence of the $E_1\alpha$ subunit of pyruvate dehydrogenase.
Figure 18:
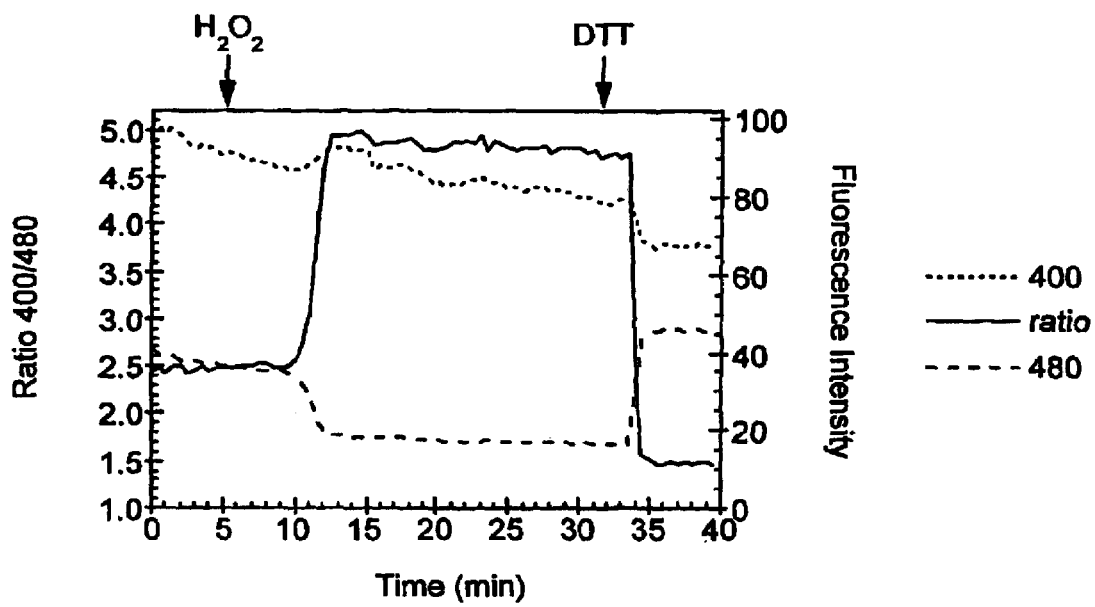
FIG. 18. Response of rosGFP1 to $H_2O_2$ and DTT induced redox potential changes in HeLa cell mitochondria. $H_2O_2$ and DTT were added at the indicted time points to a final concentration of 1 mM and 30 mM, respectively. The Fluorescence Intensity axis corresponds to the individual wavelengths, whereas the Ratio 400/480 axis corresponds to the ratio of the two wavelength channels.

To determine if redox-sensitive GFPs work as indicators of redox status within mammalian cells, rosGFP1 was expressed in the mitochondria of cultured HeLa cells. FIG. 17 shows the reticular localization pattern of rosGFP1 expressed in the mitochondrial matrix via fusion at the DNA level to the mitochondrial targeting sequence of the $E_1\alpha$ subunit of pyruvate dehydrogenase. Upon addition of an oxidizing agent ($H_2O_2$) the fluorescence excitation ratio (400 nm/490 nm) increased, as expected for an oxidation event (FIG. 18). Conversely, the addition of a reducing agent (DTT) decreased the elevated ratio to a level below the initial ratio.

From this experiment several things can be concluded. First, rosGFP1 is able to reversibly respond to induced redox changes within living cells. As seen in FIG. 18, large fluorescence changes accompany the addition of $H_2O_2$ or DTT. Second, the results demonstrate that initially rosGFP1 is not fully reduced or oxidized within mitochondria. Therefore rosGFP1 is able to detect the intrinsic redox potential inside mitochondria, presumably by interacting with endogenous oxidizing and reducing agents. Moreover, the redox potential of rosGFP1 is close to that of mitochondria and hence rosGFP1 should make an excellent probe for studying redox changes in mitochondria. Finally, given the initial fluorescence excitation ratio, the percentage of reduced to oxidized rosGFP1 could be estimated and thus the in vivo redox potential of mitochondria could be calculated.

Since redox potentials involving the liberation of $H^+$ ions are intrinsically based on pH (see Example 4), the GFP S65T/H148D variant (Wachter el al., Structure 6:1267–1277, 1998), with a $pK_a$ of 7.8, was used to examine the pH within the mitochondrion. The inherent pH sensing abilities of rosGFP2 was not utilized in this instance, due to the high pH nature of mitochondria and the high levels of autofluorescence. The fluorescence excitation ratio of GFP S65T/H148D changed as function of pH inside the mitochondrial matrix. The addition of oligomycin, carbonylcyanide-p-trifluoromethoxyphenylhydrazone (FCCP), or hydrochloric acid resulted in an acidification of the mitochondrial matrix. On the other hand, addition of $NH_4Cl$ caused the matrix pH to increase. From these types of additions, the resting pH of the mitochondrial matrix of HeLa cells was estimated to be 7.65±0.15 (n=110 cells from seven experiments). Due to a slow acidification process during the experimental setup and data collection process, this value may be an underestimate of the true mitochondrial matrix pH. Therefore, the pH value of 7.98±0.07 estimated by Llopis et al. for the mitochondrial matrix of HeLa cells was used in subsequent calculations (Llopis et al., Proc. Natl. Acad. Sci. USA 95:6803–6808, 1998).

Based on an average of 23 cells from seven independent experiments, and accounting for the 60.2 mV per pH unit change in redox potential for a reaction involving two protons (see Example 4), the redox potential in normal resting HeLa cell mitochondria was determined to be substantially more reducing than –0.3 V.

To investigate the redox potential of the cytosol, rosGFP2 was expressed in the cytosol of HeLa cells. The starting fluorescence amplitude ratio of 400/480 nm excitation was low, as expected for the reducing environment of the cytosol of healthy cells. Again, there was a marked increase and decrease in the ratio upon addition of $H_2O_2$ and DTT, respectively. However the ratio only recovered to the starting value, indicating that rosGFP2 was fully reduced in the cytosol. Hence the redox potential of the cytosol was estimated to be more reducing than –0.30 V, assuming a pH of 7.34 (Llopis et al., Proc. Natl. Acad. Sci. USA 95:6803–6808, 1998).

Example 8

Factors that Influence the Redox State of rosGFPs In vivo

It is generally thought that the major redox buffer in cells is glutathione and that the ratio of reduced glutathione (GSH) to glutathione disulfide (GSSG) is the crucial parameter for determining redox status (Meister, Methods Enzymol. 251:3–7, 1995; Deneke, Curr. Top. Cell. Regul. 36:151–180, 2000). On average, the ratio of GSH to GSSG is greater than 100:1 for whole cell determinations on a wide variety of tissue types and total glutathione levels are believed to be around 1–10 mM (Kosower and Kosower, Int. Rev. Cytol. 54:109–160, 1976; Voet and Voet, Biochemisty, 2nd ed. John Wiley & Sons, Inc., 1995, New York, N.Y.; Meister, Methods Enzymol. 251:3–7, 1995). To investigate whether glutathione may contribute to the redox state of rosGFPs in vivo, fluorescence experiments were conducted in vitro.

Incubation of reduced rosGFP1 with GSSG resulted in complete oxidation of rosGFP1 in the absence of air oxidation. From this experiment it was concluded that rosGFPs expressed in vivo can be oxidized by GSSG. However, since rosGFPs have a lower affinity for electrons than does glutathione, GSH is unable to reduce oxidized rosGFPs.

Several reports agree that the ratio of GSH to GSSG in mitochondria is between 6:1 to 33:1, with total glutathione approximately 1–2 mM (LêQuôc and LêQuôc, *Arch. Biochem. Biophys.* 273:466–478, 1989; Bindoli et al., *Arch. Biochem. Biophys.* 342:22–28, 1997; Lenton et al., *Anal. Biochem.* 274:125–130, 1999). Substituting these values into the Nernst equation (assuming a mitochondrial pH of 7.98, 37° C., and a standard redox potential of –0.205 V (Szajewski and Whitesides, *J. Am. Chem. Soc.* 102:2011–2026, 1980) for the GSH/GSSG couple) results in a mitochondrial redox potential in the range of –0.210 to –0.230 V. Since the redox potential of mitochondria is estimated to be much more reducing than –0.3 V, glutathione alone does not appear to account for such a reducing potential. Therefore, other redox active agents were investigated.

The $NAD^+$/NADH (nicotinamide adenine dinucleotide) pair was considered, because it is present at high concentrations in mitochondria and has a very reducing redox potential. The ratio of $NAD^+$ to NADH in the presence or absence of glucose has been estimated to be anywhere from 1:6 to 10:1 in mitochondria (LêQuôc and LêQuôc, *Arch. Biochem. Biophys.* 273:466–478, 1989; Ramirez et al., *Biochim. Biophys. Acta* 1273:263–267, 1996; Robinson, *Methods Enzymol.* 264:454–464, 1996). These ratios translate into redox potentials in the range of –0.328 to –0.382 V at pH 7.98 and 37° C. using –0.320 V as the standard potential of the $NAD^+$/NADH couple at pH 7. As a result, this redox couple appeared to be an ideal candidate for maintaining the very reducing environment of the mitochondrion. However, redox reactions involving nicotinamides carry out concerted two-electron transfers, whereas thiols undergo two sequential one-electron transfers. As expected, NADH was experimentally unable to directly reduce rosGFP1 in vitro.

There exists a family of pyridine nucleotide-disulfide oxidoreductases, comprising lipoamide dehydrogenases (LDH), glutathione reductases, thioredoxin reductases, trypanothione reductase, and alkylhydroperoxide reductase. These enzymes all perform homologous reactions ultimately involving the transfer of NADH or NADPH (nicotinamide adenine dinucleotide phosphate) reducing equivalents to thiols (Carothers et al., *Arch. Biochem. Biophys.* 268:409–425, 1989). In general terms, the reducing equivalents are transferred from NADH or NADPH through a concerted two-electron transfer reaction to a bound FAD (flavin adenine dinucleotide) cofactor. FAD then reduces a nearby disulfide bridge through two sequential one-electron transfer reactions. In some cases, the electrons are transferred by disulfide exchange to other nearby disulfides (Ellis and Poole, *Biochemistry* 36:13349–13356, 1997; Calzi and Poole, *Biochemisty* 36:13357–13364, 1997). Finally, the reduced pair of thiols participates in the reduction of a substrate such as lipoamide, glutathione, thioredoxin, or one of various peroxides. The key to how these enzymes carry out their electron transfer reactions is linked to the chemistry of the FAD cofactor, which is able to undergo two sequential one-electron transfers or a simultaneous two-electron transfer.

Figure 19:
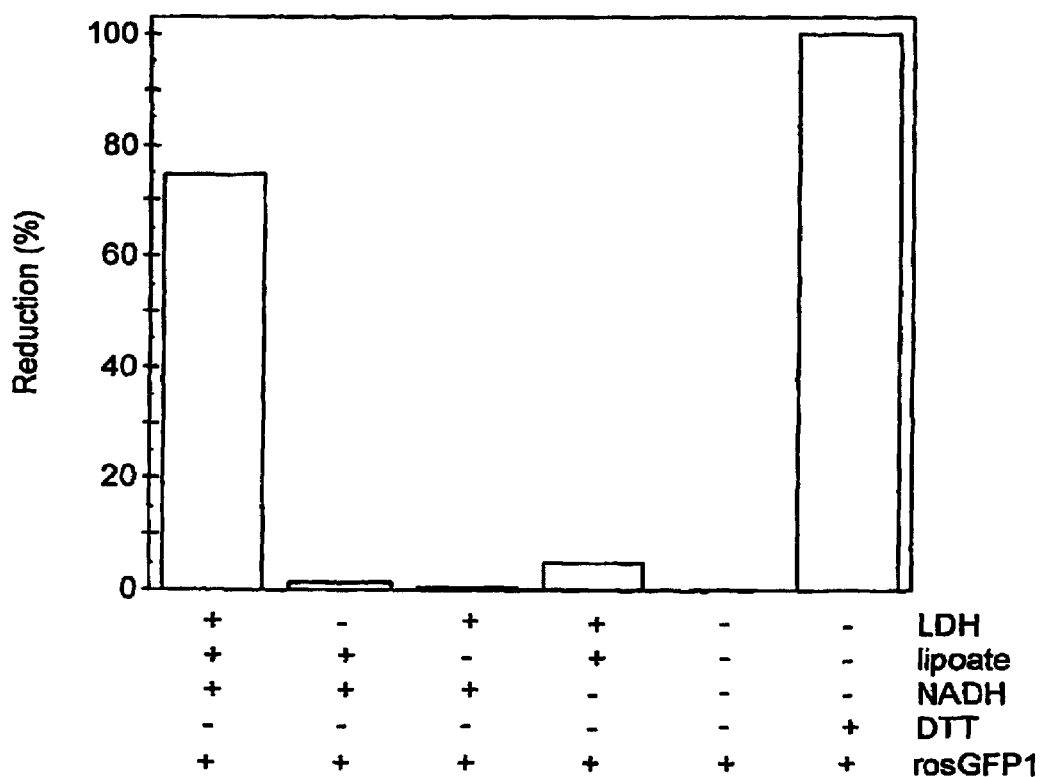
FIG. 19. NADH-dependent reduction of rosGFP1 via lipoamide dehydrogenase. Each bar represents the percent reduction of oxidized rosGFP1 by 1–2 μL LDH, 1 mM lipoate, 1 mM NADH, and/or 1 mM DTT. Samples were equilibrated at 22° C. for one hour after which the fluorescence excitation was scanned from 325 to 525 nm. Percent reduction values were determined by the fluorescence at 490 nm with 100% corresponding to reduction by DTT.

To determine if rosGFPs may be in equilibrium with agents other than just glutathione, an in vitro system analogous to a portion of the pyruvate dehydrogenase complex was set up. The system consisted of LDH, lipoate, NADH, and oxidized rosGFP1. The rationale behind this experimental setup was to monitor the reduction of rosGFP1 by NADH, through the LDH enzyme ad free lipoic acid. FIG. 19 shows that, with all four components of the system present, nearly 75% of rosGFP1 is reduced, however removal of LDH, lipoate, or NADH results in less than 5% reduction of rosGFP1. Only partial reduction was expected since the redox potential of rosGFP1 (–0.288 V) and the lipoic acid/dihydrolipoic acid couple (–0.29 V; Szajewski and Whitesides, *J. Am. Chem. Soc.* 102:2011–2026, 1980) are very similar. Air oxidized and DTT reduced rosGFP1 were used as standards for obtaining the zero and 100% values. The results of this experiment indicate that it may be possible for NADH reducing equivalents, through various enzymes such as pyruvate dehydrogenase, to be ultimately imposed on rosGFPs in vivo.

This disclosure provides redox-sensitive green fluorescent proteins (rosGFPs), nucleic acids encoding these proteins, and cells transformed with a nucleic acid encoding a rosGFP. The disclosure faker provides methods of using these molecules to analyze the redox status of, for instance, a cell or subcellular compartment. It will be apparent that the precise details of the methods described may be varied or modified without departing from the spirit of the described subject matter. We claim all such modifications and variations that fill within the scope and spirit of the claims below.

We claim:

1. An isolated mutant green fluorescent protein (GFP), with a fluorescence spectrum that is sensitive to redox status, wherein said mutant GFP shares at least 90% sequence identity with SEQ ID NO: 1 and
wherein mutations at positions corresponding to SEQ ID NO: 1 include:
   a) having a cysteine at one or both of the residues corresponding to 147 or 149 of SEQ ID NO: 1 and
   b) having a cysteine at one or both of the residues corresponding to 202 or 204 of SEQ ID NO: 1.

2. The mutant GFP of claim 1, wherein the mutations are selected from the group consisting of:
   a) the residues corresponding to 147 and 202 of SEQ ID NO: 1 are cysteine;
   b) the residues corresponding to 147 and 204 of SEQ ID NO: 1 are cysteine;
   c) the residues corresponding to 149 and 202 of SEQ ID NO: 1 are cysteine;
   d) the residues corresponding to 149 and 204 of SEQ ID NO: 1 are cysteine; and
   e) the residues corresponding to each of residues 147, 149, 202, and 204 of SEQ ID NO: 1 are cysteine.

3. The mutant GFP of claim 1, comprising an additional mutation with respect to SEQ ID NO: 1 corresponding to position 65.

4. The mutant GFP of claim 3, wherein the residue corresponding to position 65 in SEQ ID NO: 1 is threonine.

5. The mutant GFP of claim 1, wherein the fluorescence spectrum is also pH sensitive.

6. The mutant GFP of claim 1, comprising an additional mutation with respect to SEQ ID NO: 1 corresponding to position 48.

7. The mutant GFP of claim 6, wherein the residue corresponding to position 48 in SEQ ID NO: 1 is serine.

8. The mutant GFP of claim 1, comprising additional mutations with respect to SEQ ID NO: 1 corresponding to positions 48, 65, 149, and 202,
wherein the residues corresponding to positions 48, 65, 149, and 202 are serine, threonine, cysteine, and cysteine, respectively.

9. The mutant GFP of claim 1, comprising additional mutations with respect to SEQ ID NO: 1 corresponding to positions 48, 65, 149, and 204,
wherein the residues corresponding to positions 48, 65, 149, and 204 are serine, threonine, cysteine, and cysteine, respectively.

10. The mutant GFP of claim 1, comprising additional mutations with respect to SEQ ID NO: 1 corresponding to positions 48, 147, and 204,
wherein the residues corresponding to positions 48, 147, and 204 are serine, cysteine, and cysteine, respectively.

11. The mutant GFP of claim 1, comprising additional mutations with respect to SEQ ID NO: 1 corresponding to positions 48, 147, and 202,
wherein the residues corresponding to positions 48, 147, and 202 are serine, cysteine, and cysteine, respectively.

12. The mutant GFP of claim 1, comprising additional mutations with respect to SEQ ID NO: 1 corresponding to positions 48, 65, 147, 149, 202, and 204,
wherein the residues corresponding to positions 48, 65, 147, 149, 202, and 204 are serine, threonine, cysteine, cysteine, cysteine, and cysteine, respectively.

13. The mutant GFP of claim 1, comprising additional mutations with respect to SEQ ID NO: 1 corresponding to positions 48, 147, 149, 202, and 204,
wherein the residues corresponding to positions 48, 147, 149, 202, and 204 are serine, cysteine, cysteine, cysteine, and cysteine, respectively.

14. A method of analyzing an oxidation-reduction condition of or in a cell comprising:
expressing the mutant GFP of claim 1 in the cell; and
measuring fluorescence signal from the mutant GFP, thereby analyzing an oxidation-reduction condition of or in a cell.

15. The method of claim 14, wherein the mutant GFP is expressed as a fusion protein.

16. The method of claim 14, further comprising analyzing a pH condition of or in the cell using the mutant GFP.

17. The mutant GFP of claim 1, comprising an amino acid sequence as shown in SEQ ID NO: 3, SEQ ID NO: 5, SEQ ID NO: 7, SEQ ID NO: 9, SEQ ID NO: 11, or SEQ ID NO: 13.

18. A mutant GFP, with a fluorescence spectrum that is sensitive to redox status,
wherein said mutant GFP shares at least 90% sequence identity with SEQ ID NO: 1 and includes mutations selected from the group consisting of:
   a) the residues corresponding to 147 and 204 of SEQ ID NO: 1 are cysteine and cysteine, respectively;
   b) the residues corresponding to 65, 147 and 204 of SEQ ID NO: 1 are threonine, cysteine, and cysteine respectively;
   c) the residues corresponding to 149 and 202 of SEQ ID NO: 1 are cysteine and cysteine, respectively;
   d) the residues corresponding to 65, 149 and 202 of SEQ ID NO: 1 are threonine, cysteine, and cysteine respectively;

e) the residues corresponding to 147, 149, 202 and 204 of SEQ ID NO: 1 are cysteine, cysteine, cysteine and cysteine, respectively; and f) the residues corresponding to 65, 147, 149, 202 and 204 of SEQ ID NO: 1 are threonine, cysteine, cysteine, cysteine and cysteine, respectively.

19. A mutant GFP, with a fluorescence spectrum that is sensitive to redox status,
    wherein said mutant GFP shares at least 95% sequence identity with SEQ ID NO: 1 and includes mutations selected from the group consisting of:
    a) the residues corresponding to 147 and 204 of SEQ ID NO: 1 are cysteine and cysteine, respectively;
    b) the residues corresponding to 65, 147 and 204 of SEQ ID NO: 1 are threonine, cysteine, and cysteine respectively;
    c) the residues corresponding to 149 and 202 of SEQ ID NO: 1 are cysteine and cysteine, respectively;
    d) the residues corresponding to 65, 149 and 202 of SEQ ID NO: 1 are threonine, cysteine, and cysteine respectively;
    e) the residues corresponding to 147, 149, 202 and 204 of SEQ ID NO: 1 are cysteine, cysteine, cysteine and cysteine, respectively; and
    f) the residues corresponding to 65, 147, 149, 202 and 204 of SEQ ID NO: 1 are threonine, cysteine, cysteine, cysteine and cysteine, respectively.

20. An isolated mutant GFP, with a fluorescence spectrum that is sensitive to redox status,
    wherein said mutant GFP shares at least 95% sequence identity with SEQ ID NO: 1 and
    wherein mutations at positions corresponding to SEQ ID NO: 1 include:
    a) having a cysteine at one or both of the residues corresponding to 147 or 149 of SEQ ID NO: 1 and
    b) having a cysteine at one or both of the residues corresponding to 202 or 204 of SEQ ID NO: 1.

21. The mutant GFP of claim 20, wherein the mutations are selected from the group consisting of:
    a) the residues corresponding to 147 and 202 of SEQ ID NO: 1 are cysteine;
    b) the residues corresponding to 147 and 204 of SEQ ID NO: 1 are cysteine;
    c) the residues corresponding to 149 and 202 of SEQ ID NO: 1 are cysteine;
    d) the residues corresponding to 149 and 204 of SEQ ID NO: 1 are cysteine; and
    e) the residues corresponding to each of residues 147, 149, 202, and 204 of SEQ ID NO: 1 are cysteine.

22. The mutant GFP of claim 20, comprising an additional mutation with respect to SEQ ID NO: 1 corresponding to position 65.

23. The mutant GFP of claim 22, wherein the residue corresponding to position 65 in SEQ ID NO: 1 is threonine.

24. The mutant GFP of claim 20, wherein the fluorescence spectrum is also pH sensitive.

25. The mutant GFP of claim 20, comprising an additional mutation with respect to SEQ ID NO: 1 corresponding to position 48.

26. The mutant GFP of claim 25, wherein the residue corresponding to position 48 in SEQ ID NO: 1 is serine.

* * * * *

UNITED STATES PATENT AND TRADEMARK OFFICE
CERTIFICATE OF CORRECTION

| | | |
|---|---|---|
| PATENT NO. | : 7,015,310 B2 | Page 1 of 4 |
| APPLICATION NO. | : 10/471857 | |
| DATED | : March 21, 2006 | |
| INVENTOR(S) | : Remington and Hanson | |

It is certified that error appears in the above-identified patent and that said Letters Patent is hereby corrected as shown below:

On the title page, in the title, item (54), and col. 1, line 1, "OXIDATION REDUCTION" should read -- OXIDATION-REDUCTION --.

Column 2, line 63, "-0236 V" should read -- -0.236 V --

Column 2, line 65, "is method" should read -- this method --

Column 3, lines 15-22, "To overcome disadvantages ... each other" is a duplicate paragraph and should be deleted.

Column 9, line 44, "Tis protein" should read -- This protein --

Column 9, line 45, "call biology" should read -- cell biology --

Column 10, line 19, "5,625,049" should read -- 5,625,048 --

Column 10, line 19, "5,777,078" should read -- 5,777,079 --

Column 12, line 30, "May be about" should read -- may be about --

Column 12, line 59, "New York;, 1989" should read -- New York, 1989 --

Column 14, line 26, "examples am illustrative" should read -- examples are illustrative --

Column 14, line 36, "$O_2$—$^-$; HO—," should read -- $0_2 \bullet^-$, $HO \bullet$ --

Column 15, line 33, "was found Figure 2" should read -- was found. Figure 2 --

Column 16, line 29, "$E_o$, of" should read -- $E_o$ of --

Column 17, line 47, "GEP mutants" should read -- GFP mutants --

Column 18, line 6, "opted for expression" should read -- optimized for expression --

UNITED STATES PATENT AND TRADEMARK OFFICE
CERTIFICATE OF CORRECTION

PATENT NO. : 7,015,310 B2 Page 2 of 4
APPLICATION NO. : 10/471857
DATED : March 21, 2006
INVENTOR(S) : Remington and Hanson It is certified that error appears in the above-identified patent and that said Letters Patent is hereby corrected as shown below:

Column 19, Table 4,

"-- TABLE 4

| Subcellular location | Localization sequence(s) |
|---|---|
| nucleus | KKKRK |
| mitochondrion | MLRTSSLFTRRVQPSLFRNILRLQST-* |
| endoplasmic reticulum | KDEL** (providing retention in the ER) when used with a signal sequence* |
| peroxisome | SKF** |
| prenylation or insertion into plasma membrane | CaaX, CC, CXC, or CCXX** |
| cytoplasmic side of plasma membrane | fusion to SNAP-25 |
| Golgi | fusion to furin |

*amino terminal
**carboxy terminal
-- is missing the last column and should read

-- TABLE 4

| Subcellular location | Localization sequence(s) | SEQ ID NO: |
|---|---|---|
| nucleus | KKKRK | 15 |
| mitochondrion | MLRTSSLFTRRVQPSLFRNILRLQST-* | 16 |
| endoplasmic reticulum | KDEL** (providing retention in the ER) when used with a signal sequence* | 17 |
| peroxisome | SKF** | |
| prenylation or insertion into plasma membrane | CaaX, CC, CXC, or CCXX** | |
| cytoplasmic side of plasma membrane | fusion to SNAP-25 | |
| Golgi | fusion to furin | |

*amino terminal
**carboxy terminal --

Column 23, line 10, "filer purification step" should read -- further purification step --

UNITED STATES PATENT AND TRADEMARK OFFICE
CERTIFICATE OF CORRECTION

PATENT NO. : 7,015,310 B2
APPLICATION NO. : 10/471857
DATED : March 21, 2006
INVENTOR(S) : Remington and Hanson It is certified that error appears in the above-identified patent and that said Letters Patent is hereby corrected as shown below:

Column 24, line 5, "result hat indicated" should read -- result that indicated --

Column 24, line 18, "$F_{ox}$, and $F_{red}$" should read -- $F_{ox}$ and $F_{red}$ --

Column 24, line 34, "($E_{oDTT}$" should read -- ($E_{o\ DTT}$ --

Column 24, line 48, "+2H$_+$2e$^-$"should read -- +2H$^+$ +2e$^-$ --

Column 24, line 51, "[H+]$^2$" should read -- [H$^+$]$^2$ --

Column 25, line 63, "($DTT_{ox}$) Figure 5" should read -- ($DTT_{ox}$). Figure 5 --

Column 26, line 15, "non-existent The" should read -- non-existent. The --

Column 26, line 35, "$E_o^1$" should read -- $E_o'$ --

Column 26, line 43, "$DTT_{ox\ couple}$" should read -- DTT $_{ox}$ couple --

Column 26, line 44, "($E_o^1$)" should read -- ($E_o'$) --

Column 28, line 8, "at his resolution." should read -- at this resolution. --

Column 28, line 11, "ordered This" should read -- ordered. This --

Column 28, line 60, "aspartame 149" should read -- asparagine 149 --

Column 32, line 23, "enzyme ad free" should read -- enzyme and free --

Column 32, line 40, "disclosure faker provides" should read -- disclosure further provides --

UNITED STATES PATENT AND TRADEMARK OFFICE
CERTIFICATE OF CORRECTION

PATENT NO.       : 7,015,310 B2
APPLICATION NO.  : 10/471857
DATED            : March 21, 2006
INVENTOR(S)      : Remington and Hanson It is certified that error appears in the above-identified patent and that said Letters Patent is hereby corrected as shown below:

Column 32, line 46, "that fill within" should read -- that fall within --

Signed and Sealed this

Twelfth Day of June, 2007

JON W. DUDAS
*Director of the United States Patent and Trademark Office*

UNITED STATES PATENT AND TRADEMARK OFFICE
CERTIFICATE OF CORRECTION

PATENT NO. : 7,015,310 B2
APPLICATION NO. : 10/471857
DATED : March 21, 2006
INVENTOR(S) : Remington and Hanson It is certified that error appears in the above-identified patent and that said Letters Patent is hereby corrected as shown below:

On the title page, in the title, item (54), and col. 1, line 1, "OXIDATION REDUCTION" should read -- OXIDATION-REDUCTION --.

Column 2, line 63, "-0236 V" should read -- -0.236 V --

Column 2, line 65, "is method" should read -- this method --

Column 3, lines 15-22, "To overcome disadvantages ... each other" is a duplicate paragraph and should be deleted.

Column 9, line 44, "Tis protein" should read -- This protein --

Column 9, line 45, "call biology" should read -- cell biology --

Column 10, line 19, "5,625,049" should read -- 5,625,048 --

Column 10, line 19, "5,777,078" should read -- 5,777,079 --

Column 12, line 30, "May be about" should read -- may be about --

Column 12, line 59, "New York;, 1989" should read -- New York, 1989 --

Column 14, line 26, "examples am illustrative" should read -- examples are illustrative --

Column 14, line 36, "$O_2$—$^-$; HO—," should read -- $O_2^-$, HO --

Column 15, line 33, "was found Figure 2" should read -- was found. Figure 2 --

Column 16, line 29, "$E_o$, of" should read -- $E_o$ of --

Column 17, line 47, "GEP mutants" should read -- GFP mutants --

Column 18, line 6, "opted for expression" should read -- optimized for expression --

UNITED STATES PATENT AND TRADEMARK OFFICE
CERTIFICATE OF CORRECTION

PATENT NO. : 7,015,310 B2
APPLICATION NO. : 10/471857
DATED : March 21, 2006
INVENTOR(S) : Remington and Hanson It is certified that error appears in the above-identified patent and that said Letters Patent is hereby corrected as shown below:

Column 19, Table 4,

" TABLE 4

| Subcellular location | Localization sequence(s) |
|---|---|
| nucleus | KKKRK |
| mitochondrion | MLRTSSLFTRRVQPSLFRNILRLQST-* |
| endoplasmic reticulum | KDEL** (providing retention in the ER) when used with a signal sequence* |
| peroxisome | SKF** |
| prenylation or insertion into plasma membrane | CaaX, CC, CXC, or CCXX** |
| cytoplasmic side of plasma membrane | fusion to SNAP-25 |
| Golgi | fusion to furin |

*amino terminal
**carboxy terminal --

"

is missing the last column and should read

-- TABLE 4

| Subcellular location | Localization sequence(s) | SEQ ID NO: |
|---|---|---|
| nucleus | KKKRK | 15 |
| mitochondrion | MLRTSSLFTRRVQPSLFRNILRLQST-* | 16 |
| endoplasmic reticulum | KDEL** (providing retention in the ER) when used with a signal sequence* | 17 |
| peroxisome | SKF** | |
| prenylation or insertion into plasma membrane | CaaX, CC, CXC, or CCXX** | |
| cytoplasmic side of plasma membrane | fusion to SNAP-25 | |
| Golgi | fusion to furin | |

*amino terminal
**carboxy terminal --

--

Column 23, line 10, "filer purification step" should read -- further purification step --

UNITED STATES PATENT AND TRADEMARK OFFICE
CERTIFICATE OF CORRECTION

PATENT NO.        : 7,015,310 B2
APPLICATION NO. : 10/471857
DATED              : March 21, 2006
INVENTOR(S)      : Remington and Hanson It is certified that error appears in the above-identified patent and that said Letters Patent is hereby corrected as shown below:

Column 24, line 5, "result hat indicated" should read -- result that indicated --

Column 24, line 18, "$F_{ox}$, and $F_{red}$" should read -- $F_{ox}$ and $F_{red}$ --

Column 24, line 34, "($E_{oDTT}$" should read -- ($E_{o\,DTT}$ --

Column 24, line 48, "+2H$_+$2e$^-$"should read -- +2H$^+$ +2e$^-$--

Column 24, line 51, "[H+]$^2$" should read -- [H$^+$]$^2$ --

Column 25, line 63, "(DTT$_{ox}$) Figure 5" should read -- (DTT$_{ox}$). Figure 5 --

Column 26, line 15, "non-existent The" should read -- non-existent. The --

Column 26, line 35, "$E_o^1$" should read -- $E_o'$ --

Column 26, line 43, "DTT$_{ox\,couple}$" should read -- DTT$_{ox}$ couple --

Column 26, line 44, "($E_o^1$)" should read -- ($E_o'$) --

Column 28, line 8, "at his resolution." should read -- at this resolution. --

Column 28, line 11, "ordered This" should read -- ordered. This --

Column 28, line 60, "aspartame 149" should read -- asparagine 149 --

Column 32, line 23, "enzyme ad free" should read -- enzyme and free --

Column 32, line 40, "disclosure faker provides" should read -- disclosure further provides --

UNITED STATES PATENT AND TRADEMARK OFFICE
CERTIFICATE OF CORRECTION

PATENT NO. : 7,015,310 B2
APPLICATION NO. : 10/471857
DATED : March 21, 2006
INVENTOR(S) : Remington and Hanson It is certified that error appears in the above-identified patent and that said Letters Patent is hereby corrected as shown below:

Column 32, line 46, "that fill within" should read -- that fall within --

This certificate supersedes Certificate of Correction issued June 12, 2007.

Signed and Sealed this

Second Day of October, 2007

JON W. DUDAS
*Director of the United States Patent and Trademark Office*

SEQUENCE LISTING

<160> NUMBER OF SEQ ID NOS: 13

<210> SEQ ID NO 1
<211> LENGTH: 238
<212> TYPE: PRT
<213> ORGANISM: Aequorea victoria

<400> SEQUENCE: 1

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

```
Thr Thr Gly Lys Leu Pro Val Pro Trp Pro Thr Leu Val Thr Thr Phe
        50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Tyr Lys Asp Asp Gly Asn Tyr Lys Ser Arg Ala Glu Val
            100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Met Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Ile Leu Leu Glu Phe Val
            210                 215                 220

Thr Ala Ala Gly Ile Thr His Gly Met Asp Glu Leu Tyr Lys
225                 230                 235

<210> SEQ ID NO 2
<211> LENGTH: 717
<212> TYPE: DNA
<213> ORGANISM: Artificial Sequence
<220> FEATURE:
<223> OTHER INFORMATION: Variant derived from A. victoria
<220> FEATURE:
<221> NAME/KEY: CDS
<222> LOCATION: (1)..(717)

<400> SEQUENCE: 2 atg agt aaa gga gaa gaa ctt ttc act gga gtt gtc cca att ctt gtt     48
Met Ser Lys Gly Glu Glu Leu Phe Thr Gly Val Val Pro Ile Leu Val
 1               5                  10                  15 gaa tta gat ggt gat gtt aat ggg cac aaa ttt tct gtc agt gga gag    96
Glu Leu Asp Gly Asp Val Asn Gly His Lys Phe Ser Val Ser Gly Glu
             20                  25                  30 ggt gaa ggt gat gca aca tac gga aaa ctt acc ctt aaa ttt att tcc   144
Gly Glu Gly Asp Ala Thr Tyr Gly Lys Leu Thr Leu Lys Phe Ile Ser
         35                  40                  45 act act gga aaa cta cct gtt cca tgg cca aca ctt gtc act act ttc   192
Thr Thr Gly Lys Leu Pro Val Pro Trp Pro Thr Leu Val Thr Thr Phe
     50                  55                  60 act tat ggt gtt caa tgc ttt tca aga tac cca gat cat atg aaa cgg   240
Thr Tyr Gly Val Gln Cys Phe Ser Arg Tyr Pro Asp His Met Lys Arg
 65                  70                  75                  80 cat gac ttt ttc aag agt gcc atg ccc gaa ggt tat gta cag gaa aga   288
His Asp Phe Phe Lys Ser Ala Met Pro Glu Gly Tyr Val Gln Glu Arg
                 85                  90                  95 act ata ttt ttc aaa gat gac ggg aac tac aag aca cgt gct gaa gtc   336
Thr Ile Phe Phe Lys Asp Asp Gly Asn Tyr Lys Thr Arg Ala Glu Val
            100                 105                 110 aag ttt gaa ggt gat acc ctt gtt aat aga atc gag tta aaa ggt att   384
```

```
Lys Phe Glu Gly Asp Thr Leu Val Asn Arg Ile Glu Leu Lys Gly Ile
            115                 120                 125 gat ttt aaa gaa gat gga aac att ctt gga cac aaa ttg gaa tac aac        432
Asp Phe Lys Glu Asp Gly Asn Ile Leu Gly His Lys Leu Glu Tyr Asn
        130                 135                 140 tat aac tgc cac aat gta tac atc atg gca gac aaa caa aag aat gga        480
Tyr Asn Cys His Asn Val Tyr Ile Met Ala Asp Lys Gln Lys Asn Gly
145                 150                 155                 160 atc aaa gtt aac ttc aaa att aga cac aac att gaa gat gga agc gtt        528
Ile Lys Val Asn Phe Lys Ile Arg His Asn Ile Glu Asp Gly Ser Val
                165                 170                 175 caa cta gca gac cat tat caa caa aat act cca att ggc gat ggc cct        576
Gln Leu Ala Asp His Tyr Gln Gln Asn Thr Pro Ile Gly Asp Gly Pro
            180                 185                 190 gtc ctt tta cca gac aac cat tac ctg tcc aca tgc tct gcc ctt tcg        624
Val Leu Leu Pro Asp Asn His Tyr Leu Ser Thr Cys Ser Ala Leu Ser
        195                 200                 205 aaa gat ccc aac gaa aag aga gac cac atg gtc ctt ctt gag ttt gta        672
Lys Asp Pro Asn Glu Lys Arg Asp His Met Val Leu Leu Glu Phe Val
210                 215                 220 aca gct gct ggg att aca cat ggc atg gat gaa cta tac aaa taa            717
Thr Ala Ala Gly Ile Thr His Gly Met Asp Glu Leu Tyr Lys
225                 230                 235

<210> SEQ ID NO 3
<211> LENGTH: 238
<212> TYPE: PRT
<213> ORGANISM: Artificial Sequence
<220> FEATURE:
<223> OTHER INFORMATION: Variant derived from A. victoria

<400> SEQUENCE: 3

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Ser
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Cys His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Cys Ser Ala Leu Ser
        195                 200                 205
```

```
Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 4
<211> LENGTH: 717
<212> TYPE: DNA
<213> ORGANISM: Artificial sequence
<220> FEATURE:
<223> OTHER INFORMATION: Variant derived from A. victoria
<220> FEATURE:
<221> NAME/KEY: CDS
<222> LOCATION: (1)..(717)

<400> SEQUENCE: 4 atg agt aaa gga gaa gaa ctt ttc act gga gtt gtc cca att ctt gtt      48
Met Ser Lys Gly Glu Glu Leu Phe Thr Gly Val Val Pro Ile Leu Val
1               5                   10                  15 gaa tta gat ggt gat gtt aat ggg cac aaa ttt tct gtc agt gga gag      96
Glu Leu Asp Gly Asp Val Asn Gly His Lys Phe Ser Val Ser Gly Glu
            20                  25                  30 ggt gaa ggt gat gca aca tac gga aaa ctt acc ctt aaa ttt att tcc     144
Gly Glu Gly Asp Ala Thr Tyr Gly Lys Leu Thr Leu Lys Phe Ile Ser
        35                  40                  45 act act gga aaa cta cct gtt cca tgg cca aca ctt gtc act act ttc     192
Thr Thr Gly Lys Leu Pro Val Pro Trp Pro Thr Leu Val Thr Thr Phe
    50                  55                  60 tct tat ggt gtt caa tgc ttt tca aga tac cca gat cat atg aaa cgg     240
Ser Tyr Gly Val Gln Cys Phe Ser Arg Tyr Pro Asp His Met Lys Arg
65                  70                  75                  80 cat gac ttt ttc aag agt gcc atg ccc gaa ggt tat gta cag gaa aga     288
His Asp Phe Phe Lys Ser Ala Met Pro Glu Gly Tyr Val Gln Glu Arg
                85                  90                  95 act ata ttt ttc aaa gat gac ggg aac tac aag aca cgt gct gaa gtc     336
Thr Ile Phe Phe Lys Asp Asp Gly Asn Tyr Lys Thr Arg Ala Glu Val
            100                 105                 110 aag ttt gaa ggt gat acc ctt gtt aat aga atc gag tta aaa ggt att     384
Lys Phe Glu Gly Asp Thr Leu Val Asn Arg Ile Glu Leu Lys Gly Ile
        115                 120                 125 gat ttt aaa gaa gat gga aac att ctt gga cac aaa ttg gaa tac aac     432
Asp Phe Lys Glu Asp Gly Asn Ile Leu Gly His Lys Leu Glu Tyr Asn
    130                 135                 140 tat aac tgc cac aat gta tac atc atg gca gac aaa caa aag aat gga     480
Tyr Asn Cys His Asn Val Tyr Ile Met Ala Asp Lys Gln Lys Asn Gly
145                 150                 155                 160 atc aaa gtt aac ttc aaa att aga cac aac att gaa gat gga agc gtt     528
Ile Lys Val Asn Phe Lys Ile Arg His Asn Ile Glu Asp Gly Ser Val
                165                 170                 175 caa cta gca gac cat tat caa caa aat act cca att ggc gat ggc cct     576
Gln Leu Ala Asp His Tyr Gln Gln Asn Thr Pro Ile Gly Asp Gly Pro
            180                 185                 190 gtc ctt tta cca gac aac cat tac ctg tcc aca tgc tct gcc ctt tcg     624
Val Leu Leu Pro Asp Asn His Tyr Leu Ser Thr Cys Ser Ala Leu Ser
        195                 200                 205 aaa gat ccc aac gaa aag aga gac cac atg gtc ctt ctt gag ttt gta     672
Lys Asp Pro Asn Glu Lys Arg Asp His Met Val Leu Leu Glu Phe Val
    210                 215                 220 aca gct gct ggg att aca cat ggc atg gat gaa cta tac aaa taa        717
Thr Ala Ala Gly Ile Thr His Gly Met Asp Glu Leu Tyr Lys
225                 230                 235
```

<210> SEQ ID NO 5
<211> LENGTH: 238
<212> TYPE: PRT
<213> ORGANISM: Artificial sequence
<220> FEATURE:
<223> OTHER INFORMATION: Variant derived from A. victoria

<400> SEQUENCE: 5

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Ser
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Cys His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Cys Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 6
<211> LENGTH: 717
<212> TYPE: DNA
<213> ORGANISM: Artificial sequence
<220> FEATURE:
<223> OTHER INFORMATION: Variant derived from A. victoria
<220> FEATURE:
<221> NAME/KEY: CDS
<222> LOCATION: (1)..(717)

<400> SEQUENCE: 6

```
atg agt aaa gga gaa gaa ctt ttc act gga gtt gtc cca att ctt gtt    48
Met Ser Lys Gly Glu Glu Leu Phe Thr Gly Val Val Pro Ile Leu Val
1               5                   10                  15 gaa tta gat ggt gat gtt aat ggg cac aaa ttt tct gtc agt gga gag    96
Glu Leu Asp Gly Asp Val Asn Gly His Lys Phe Ser Val Ser Gly Glu
            20                  25                  30 ggt gaa ggt gat gca aca tac gga aaa ctt acc ctt aaa ttt att tcc   144
Gly Glu Gly Asp Ala Thr Tyr Gly Lys Leu Thr Leu Lys Phe Ile Ser
```

```
act act gga aaa cta cct gtt cca tgg cca aca ctt gtc act act ttc      192
Thr Thr Gly Lys Leu Pro Val Pro Trp Pro Thr Leu Val Thr Thr Phe
 50                  55                  60 act tat ggt gtt caa tgc ttt tca aga tac cca gat cat atg aaa cgg      240
Thr Tyr Gly Val Gln Cys Phe Ser Arg Tyr Pro Asp His Met Lys Arg
 65                  70                  75                  80 cat gac ttt ttc aag agt gcc atg ccc gaa ggt tat gta cag gaa aga      288
His Asp Phe Phe Lys Ser Ala Met Pro Glu Gly Tyr Val Gln Glu Arg
                     85                  90                  95 act ata ttt ttc aaa gat gac ggg aac tac aag aca cgt gct gaa gtc      336
Thr Ile Phe Phe Lys Asp Asp Gly Asn Tyr Lys Thr Arg Ala Glu Val
                100                 105                 110 aag ttt gaa ggt gat acc ctt gtt aat aga atc gag tta aaa ggt att      384
Lys Phe Glu Gly Asp Thr Leu Val Asn Arg Ile Glu Leu Lys Gly Ile
            115                 120                 125 gat ttt aaa gaa gat gga aac att ctt gga cac aaa ttg gaa tac aac      432
Asp Phe Lys Glu Asp Gly Asn Ile Leu Gly His Lys Leu Glu Tyr Asn
130                 135                 140 tat aac tca cac tgt gta tac atc atg gca gac aaa caa aag aat gga      480
Tyr Asn Ser His Cys Val Tyr Ile Met Ala Asp Lys Gln Lys Asn Gly
145                 150                 155                 160 atc aaa gtt aac ttc aaa att aga cac aac att gaa gat gga agc gtt      528
Ile Lys Val Asn Phe Lys Ile Arg His Asn Ile Glu Asp Gly Ser Val
                165                 170                 175 caa cta gca gac cat tat caa caa aat act cca att ggc gat ggc cct      576
Gln Leu Ala Asp His Tyr Gln Gln Asn Thr Pro Ile Gly Asp Gly Pro
            180                 185                 190 gtc ctt tta cca gac aac cat tac ctg tgc aca caa tct gcc ctt tcg      624
Val Leu Leu Pro Asp Asn His Tyr Leu Cys Thr Gln Ser Ala Leu Ser
        195                 200                 205 aaa gat ccc aac gaa aag aga gac cac atg gtc ctt ctt gag ttt gta      672
Lys Asp Pro Asn Glu Lys Arg Asp His Met Val Leu Leu Glu Phe Val
    210                 215                 220 aca gct gct ggg att aca cat ggc atg gat gaa cta tac aaa taa          717
Thr Ala Ala Gly Ile Thr His Gly Met Asp Glu Leu Tyr Lys
225                 230                 235
```

<210> SEQ ID NO 7
<211> LENGTH: 238
<212> TYPE: PRT
<213> ORGANISM: Artificial sequence
<220> FEATURE:
<223> OTHER INFORMATION: Variant derived from A. victoria

<400> SEQUENCE: 7

```
Met Ser Lys Gly Glu Glu Leu Phe Thr Gly Val Val Pro Ile Leu Val
  1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Ser
         35                  40                  45

Thr Thr Gly Lys Leu Pro Val Pro Trp Pro Thr Leu Val Thr Thr Phe
 50                  55                  60

Thr Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
```

```
                    100                 105                 110
Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Ser His Cys Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Cys Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 8
<211> LENGTH: 717
<212> TYPE: DNA
<213> ORGANISM: Artificial sequence
<220> FEATURE:
<223> OTHER INFORMATION: Variant derived from A. victoria
<220> FEATURE:
<221> NAME/KEY: CDS
<222> LOCATION: (1)..(717)

<400> SEQUENCE: 8

```
atg agt aaa gga gaa gaa ctt ttc act gga gtt gtc cca att ctt gtt      48
Met Ser Lys Gly Glu Glu Leu Phe Thr Gly Val Val Pro Ile Leu Val
1               5                   10                  15 gaa tta gat ggt gat gtt aat ggg cac aaa ttt tct gtc agt gga gag      96
Glu Leu Asp Gly Asp Val Asn Gly His Lys Phe Ser Val Ser Gly Glu
            20                  25                  30 ggt gaa ggt gat gca aca tac gga aaa ctt acc ctt aaa ttt att tcc     144
Gly Glu Gly Asp Ala Thr Tyr Gly Lys Leu Thr Leu Lys Phe Ile Ser
        35                  40                  45 act act gga aaa cta cct gtt cca tgg cca aca ctt gtc act act ttc     192
Thr Thr Gly Lys Leu Pro Val Pro Trp Pro Thr Leu Val Thr Thr Phe
    50                  55                  60 tct tat ggt gtt caa tgc ttt tca aga tac cca gat cat atg aaa cgg     240
Ser Tyr Gly Val Gln Cys Phe Ser Arg Tyr Pro Asp His Met Lys Arg
65                  70                  75                  80 cat gac ttt ttc aag agt gcc atg ccc gaa ggt tat gta cag gaa aga     288
His Asp Phe Phe Lys Ser Ala Met Pro Glu Gly Tyr Val Gln Glu Arg
                85                  90                  95 act ata ttt ttc aaa gat gac ggg aac tac aag aca cgt gct gaa gtc     336
Thr Ile Phe Phe Lys Asp Asp Gly Asn Tyr Lys Thr Arg Ala Glu Val
            100                 105                 110 aag ttt gaa ggt gat acc ctt gtt aat aga atc gag tta aaa ggt att     384
Lys Phe Glu Gly Asp Thr Leu Val Asn Arg Ile Glu Leu Lys Gly Ile
        115                 120                 125 gat ttt aaa gaa gat gga aac att ctt gga cac aaa ttg gaa tac aac     432
Asp Phe Lys Glu Asp Gly Asn Ile Leu Gly His Lys Leu Glu Tyr Asn
    130                 135                 140 tat aac tca cac tgt gta tac atc atg gca gac aaa caa aag aat gga     480
Tyr Asn Ser His Cys Val Tyr Ile Met Ala Asp Lys Gln Lys Asn Gly
145                 150                 155                 160
```

```
atc aaa gtt aac ttc aaa att aga cac aac att gaa gat gga agc gtt      528
Ile Lys Val Asn Phe Lys Ile Arg His Asn Ile Glu Asp Gly Ser Val
            165                 170                 175 caa cta gca gac cat tat caa caa aat act cca att ggc gat ggc cct      576
Gln Leu Ala Asp His Tyr Gln Gln Asn Thr Pro Ile Gly Asp Gly Pro
        180                 185                 190 gtc ctt tta cca gac aac cat tac ctg tgc aca caa tct gcc ctt tcg      624
Val Leu Leu Pro Asp Asn His Tyr Leu Cys Thr Gln Ser Ala Leu Ser
    195                 200                 205 aaa gat ccc aac gaa aag aga gac cac atg gtc ctt ctt gag ttt gta      672
Lys Asp Pro Asn Glu Lys Arg Asp His Met Val Leu Leu Glu Phe Val
210                 215                 220 aca gct gct ggg att aca cat ggc atg gat gaa cta tac aaa taa          717
Thr Ala Ala Gly Ile Thr His Gly Met Asp Glu Leu Tyr Lys
225                 230                 235

<210> SEQ ID NO 9
<211> LENGTH: 238
<212> TYPE: PRT
<213> ORGANISM: Artificial sequence
<220> FEATURE:
<223> OTHER INFORMATION: Variant derived from A. victoria

<400> SEQUENCE: 9
```

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Ser
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Cys Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Cys Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 10
<211> LENGTH: 717
<212> TYPE: DNA

```
<213> ORGANISM: Artificial sequence
<220> FEATURE:
<223> OTHER INFORMATION: Variant derived from A. victoria
<220> FEATURE:
<221> NAME/KEY: CDS
<222> LOCATION: (1)..(717)

<400> SEQUENCE: 10 atg agt aaa gga gaa gaa ctt ttc act gga gtt gtc cca att ctt gtt      48
Met Ser Lys Gly Glu Glu Leu Phe Thr Gly Val Val Pro Ile Leu Val
1               5                   10                  15 gaa tta gat ggt gat gtt aat ggg cac aaa ttt tct gtc agt gga gag      96
Glu Leu Asp Gly Asp Val Asn Gly His Lys Phe Ser Val Ser Gly Glu
            20                  25                  30 ggt gaa ggt gat gca aca tac gga aaa ctt acc ctt aaa ttt att tcc     144
Gly Glu Gly Asp Ala Thr Tyr Gly Lys Leu Thr Leu Lys Phe Ile Ser
        35                  40                  45 act act gga aaa cta cct gtt cca tgg cca aca ctt gtc act act ttc     192
Thr Thr Gly Lys Leu Pro Val Pro Trp Pro Thr Leu Val Thr Thr Phe
    50                  55                  60 act tat ggt gtt caa tgc ttt tca aga tac cca gat cat atg aaa cgg     240
Thr Tyr Gly Val Gln Cys Phe Ser Arg Tyr Pro Asp His Met Lys Arg
65                  70                  75                  80 cat gac ttt ttc aag agt gcc atg ccc gaa ggt tat gta cag gaa aga     288
His Asp Phe Phe Lys Ser Ala Met Pro Glu Gly Tyr Val Gln Glu Arg
                85                  90                  95 act ata ttt ttc aaa gat gac ggg aac tac aag aca cgt gct gaa gtc     336
Thr Ile Phe Phe Lys Asp Asp Gly Asn Tyr Lys Thr Arg Ala Glu Val
            100                 105                 110 aag ttt gaa ggt gat acc ctt gtt aat aga atc gag tta aaa ggt att     384
Lys Phe Glu Gly Asp Thr Leu Val Asn Arg Ile Glu Leu Lys Gly Ile
        115                 120                 125 gat ttt aaa gaa gat gga aac att ctt gga cac aaa ttg gaa tac aac     432
Asp Phe Lys Glu Asp Gly Asn Ile Leu Gly His Lys Leu Glu Tyr Asn
    130                 135                 140 tat aac tgc cac tgt gta tac atc atg gca gac aaa caa aag aat gga     480
Tyr Asn Cys His Cys Val Tyr Ile Met Ala Asp Lys Gln Lys Asn Gly
145                 150                 155                 160 atc aaa gtt aac ttc aaa att aga cac aac att gaa gat gga agc gtt     528
Ile Lys Val Asn Phe Lys Ile Arg His Asn Ile Glu Asp Gly Ser Val
                165                 170                 175 caa cta gca gac cat tat caa caa aat act cca att ggc gat ggc cct     576
Gln Leu Ala Asp His Tyr Gln Gln Asn Thr Pro Ile Gly Asp Gly Pro
            180                 185                 190 gtc ctt tta cca gac aac cat tac ctg tgc aca tgc tct gcc ctt tcg     624
Val Leu Leu Pro Asp Asn His Tyr Leu Cys Thr Cys Ser Ala Leu Ser
        195                 200                 205 aaa gat ccc aac gaa aag aga gac cac atg gtc ctt ctt gag ttt gta     672
Lys Asp Pro Asn Glu Lys Arg Asp His Met Val Leu Leu Glu Phe Val
    210                 215                 220 aca gct gct ggg att aca cat ggc atg gat gaa cta tac aaa taa         717
Thr Ala Ala Gly Ile Thr His Gly Met Asp Glu Leu Tyr Lys
225                 230                 235

<210> SEQ ID NO 11
<211> LENGTH: 238
<212> TYPE: PRT
<213> ORGANISM: Artificial sequence
<220> FEATURE:
<223> OTHER INFORMATION: Variant derived from A. victoria

<400> SEQUENCE: 11
```

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Ser
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Cys His Cys Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Cys Thr Cys Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 12
<211> LENGTH: 717
<212> TYPE: DNA
<213> ORGANISM: Artificial sequence
<220> FEATURE:
<223> OTHER INFORMATION: Variant derived from A. victoria
<220> FEATURE:
<221> NAME/KEY: CDS
<222> LOCATION: (1)..(717)

<400> SEQUENCE: 12

```
atg agt aaa gga gaa gaa ctt ttc act gga gtt gtc cca att ctt gtt      48
Met Ser Lys Gly Glu Glu Leu Phe Thr Gly Val Val Pro Ile Leu Val
1               5                   10                  15 gaa tta gat ggt gat gtt aat ggg cac aaa ttt tct gtc agt gga gag      96
Glu Leu Asp Gly Asp Val Asn Gly His Lys Phe Ser Val Ser Gly Glu
            20                  25                  30 ggt gaa ggt gat gca aca tac gga aaa ctt acc ctt aaa ttt att tcc     144
Gly Glu Gly Asp Ala Thr Tyr Gly Lys Leu Thr Leu Lys Phe Ile Ser
        35                  40                  45 act act gga aaa cta cct gtt cca tgg cca aca ctt gtc act act ttc     192
Thr Thr Gly Lys Leu Pro Val Pro Trp Pro Thr Leu Val Thr Thr Phe
    50                  55                  60 tct tat ggt gtt caa tgc ttt tca aga tac cca gat cat atg aaa cgg     240
Ser Tyr Gly Val Gln Cys Phe Ser Arg Tyr Pro Asp His Met Lys Arg
65                  70                  75                  80 cat gac ttt ttc aag agt gcc atg ccc gaa ggt tat gta cag gaa aga     288
```

-continued

```
His Asp Phe Phe Lys Ser Ala Met Pro Glu Gly Tyr Val Gln Glu Arg
             85                  90                  95 act ata ttt ttc aaa gat gac ggg aac tac aag aca cgt gct gaa gtc    336
Thr Ile Phe Phe Lys Asp Asp Gly Asn Tyr Lys Thr Arg Ala Glu Val
            100                 105                 110 aag ttt gaa ggt gat acc ctt gtt aat aga atc gag tta aaa ggt att    384
Lys Phe Glu Gly Asp Thr Leu Val Asn Arg Ile Glu Leu Lys Gly Ile
            115                 120                 125 gat ttt aaa gaa gat gga aac att ctt gga cac aaa ttg gaa tac aac    432
Asp Phe Lys Glu Asp Gly Asn Ile Leu Gly His Lys Leu Glu Tyr Asn
        130                 135                 140 tat aac tgc cac tgt gta tac atc atg gca gac aaa caa aag aat gga    480
Tyr Asn Cys His Cys Val Tyr Ile Met Ala Asp Lys Gln Lys Asn Gly
145                 150                 155                 160 atc aaa gtt aac ttc aaa att aga cac aac att gaa gat gga agc gtt    528
Ile Lys Val Asn Phe Lys Ile Arg His Asn Ile Glu Asp Gly Ser Val
                165                 170                 175 caa cta gca gac cat tat caa caa aat act cca att ggc gat ggc cct    576
Gln Leu Ala Asp His Tyr Gln Gln Asn Thr Pro Ile Gly Asp Gly Pro
            180                 185                 190 gtc ctt tta cca gac aac cat tac ctg tgc aca tgc tct gcc ctt tcg    624
Val Leu Leu Pro Asp Asn His Tyr Leu Cys Thr Cys Ser Ala Leu Ser
        195                 200                 205 aaa gat ccc aac gaa aag aga gac cac atg gtc ctt ctt gag ttt gta    672
Lys Asp Pro Asn Glu Lys Arg Asp His Met Val Leu Leu Glu Phe Val
    210                 215                 220 aca gct gct ggg att aca cat ggc atg gat gaa cta tac aaa taa        717
Thr Ala Ala Gly Ile Thr His Gly Met Asp Glu Leu Tyr Lys
225                 230                 235
```

<210> SEQ ID NO 13
<211> LENGTH: 238
<212> TYPE: PRT
<213> ORGANISM: Artificial sequence
<220> FEATURE:
<223> OTHER INFORMATION: Variant derived from A. victoria

<400> SEQUENCE: 13

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Ser
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Cys His Cys Val Tyr Ile Met Ala Asp Lys Gln Lys Asn Gly
145                 150                 155                 160
```

-continued

```
Ile Lys Val Asn Phe Lys Ile Arg His Asn Ile Glu Asp Gly Ser Val
                165             170             175

Gln Leu Ala Asp His Tyr Gln Gln Asn Thr Pro Ile Gly Asp Gly Pro
            180             185             190

Val Leu Leu Pro Asp Asn His Tyr Leu Cys Thr Cys Ser Ala Leu Ser
        195             200             205

Lys Asp Pro Asn Glu Lys Arg Asp His Met Val Leu Leu Glu Phe Val
    210             215             220

Thr Ala Ala Gly Ile Thr His Gly Met Asp Glu Leu Tyr Lys
225             230             235
```